(12) United States Patent
Dell et al.

(10) Patent No.: US 6,770,830 B2
(45) Date of Patent: Aug. 3, 2004

(54) RADIOACTIVE SEED SORTER AND METHOD FOR SORTING RADIOACTIVE SEEDS

(75) Inventors: Mary Anne Dell, Pittsburgh, PA (US); Erik Witt, Mahwah, NJ (US); Jessica Bede, New York, NY (US); Charles Thiele, Butler, PA (US)

(73) Assignee: Capintec, Inc., Ramsey, NJ (US)

( * ) Notice: Subject to any disclaimer, the term of this patent is extended or adjusted under 35 U.S.C. 154(b) by 141 days.

(21) Appl. No.: 10/222,189

(22) Filed: Aug. 15, 2002

(65) Prior Publication Data

US 2004/0034268 A1 Feb. 19, 2004

(51) Int. Cl.[7] .............................................. B07C 5/00
(52) U.S. Cl. ...................................................... 209/576
(58) Field of Search ................................. 209/576, 589

(56) References Cited

U.S. PATENT DOCUMENTS

| | | | | | |
|---|---|---|---|---|---|
| 4,144,970 A | * | 3/1979 | McKnight et al. | .......... | 209/542 |
| 4,194,634 A | * | 3/1980 | Kelly | .......... | 209/589 |
| 4,372,941 A | * | 2/1983 | Ryan | .......... | 435/15 |
| 4,445,615 A | * | 5/1984 | Bohme et al. | .......... | 209/555 |
| 4,576,286 A | * | 3/1986 | Buckley et al. | .......... | 209/558 |
| 4,646,978 A | * | 3/1987 | Johnson et al. | .......... | 241/24.12 |
| 4,653,081 A | * | 3/1987 | Sipila et al. | .......... | 378/45 |
| 4,759,345 A | * | 7/1988 | Mistry | .......... | 600/8 |
| 5,076,502 A | * | 12/1991 | Kitaguchi et al. | .......... | 241/36 |
| 5,628,410 A | * | 5/1997 | Smith et al. | .......... | 209/579 |
| 5,906,574 A | * | 5/1999 | Kan | .......... | 600/7 |
| 6,106,455 A | * | 8/2000 | Kan | .......... | 600/7 |
| 6,113,529 A | * | 9/2000 | Shi | .......... | 600/7 |
| 6,248,968 B1 | * | 6/2001 | Suzuki et al. | .......... | 209/576 |
| 6,324,253 B1 | * | 11/2001 | Yuyama et al. | .......... | 378/57 |
| 6,565,502 B1 | * | 5/2003 | Bede et al. | .......... | 600/7 |
| 6,582,354 B2 | * | 6/2003 | Ellard | .......... | 600/8 |
| 6,599,233 B1 | * | 7/2003 | Bede et al. | .......... | 600/7 |
| 6,638,206 B2 | * | 10/2003 | Green et al. | .......... | 600/7 |

FOREIGN PATENT DOCUMENTS

WO        WO0074073 A    *    7/2000    ............ G21G/4/08

* cited by examiner

*Primary Examiner*—Donald P. Walsh
*Assistant Examiner*—Matthew J. Kohner
(74) *Attorney, Agent, or Firm*—Martin Fleit; Paul D. Bianco; Fleit Kain Gibbons Gutman Bongini & Bianco, PL

(57) ABSTRACT

Method and apparatus for assaying and sorting radioactive seeds that provides for feeding seeds in line horizontally in end to end fashion; translating the seeds from the horizontal to a vertical stack; singulating the seeds from the vertical stack and moving a singulated seed to a horizontally displaced position; loading the horizontally displaced singulated seed into a shuttle by pushing vertically downward into a cavity in the shuttle; moving the shuttle horizontally from a retracted position where it receives a singulated seed, into one end of an annular dose calibrator to an intermediate position within the dose calibrator and out of the other end of the annular dose calibrator to an unloader position; determining the activity of the singulated seed contained in the cavity while it is in the intermediate position; dropping the singulated seed into one of a plurality of receptacles at the unloader position; and controlling the plurality of receptacles to position a preselected receptacle to receive the singulated seed based on the activity determined.

20 Claims, 19 Drawing Sheets

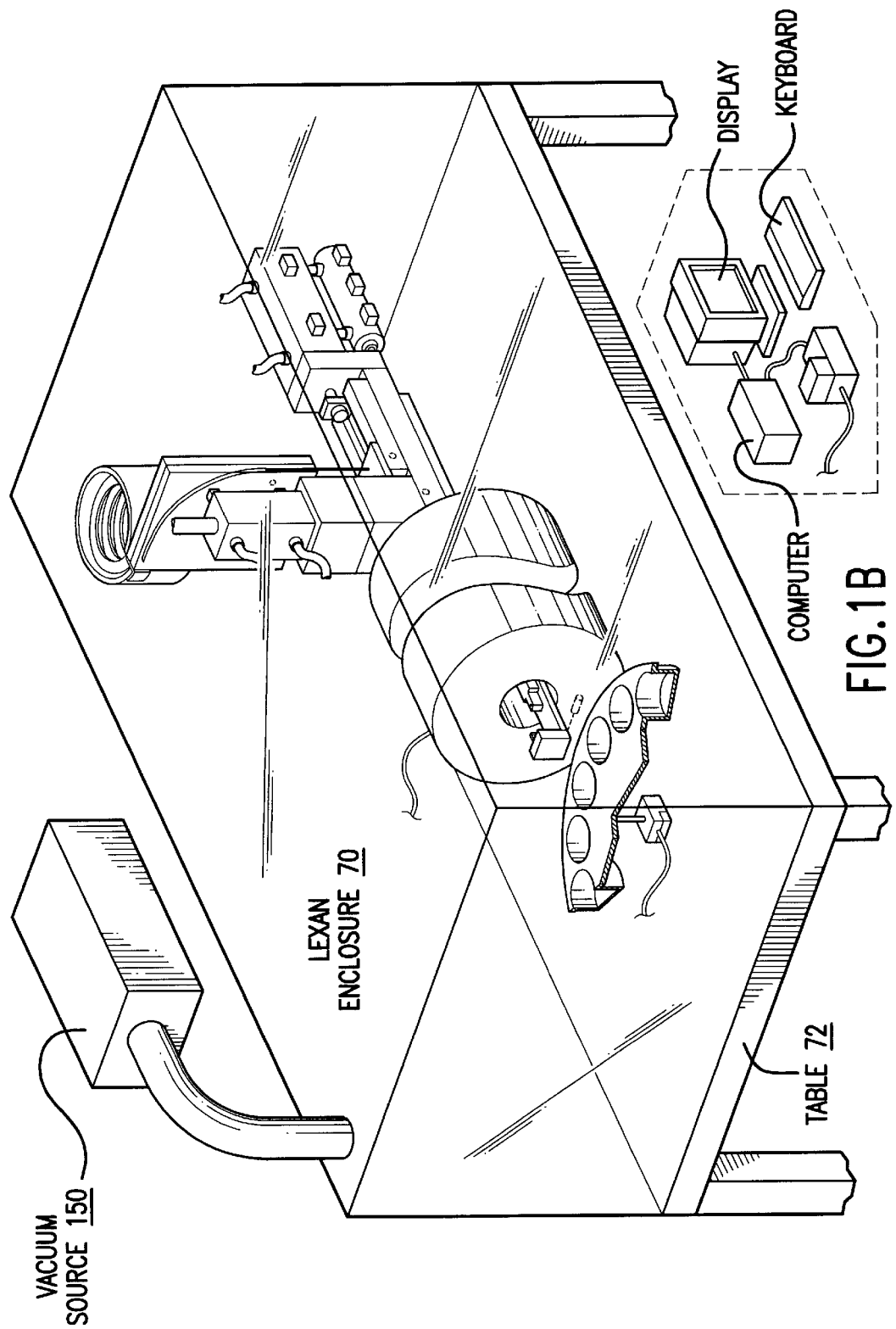

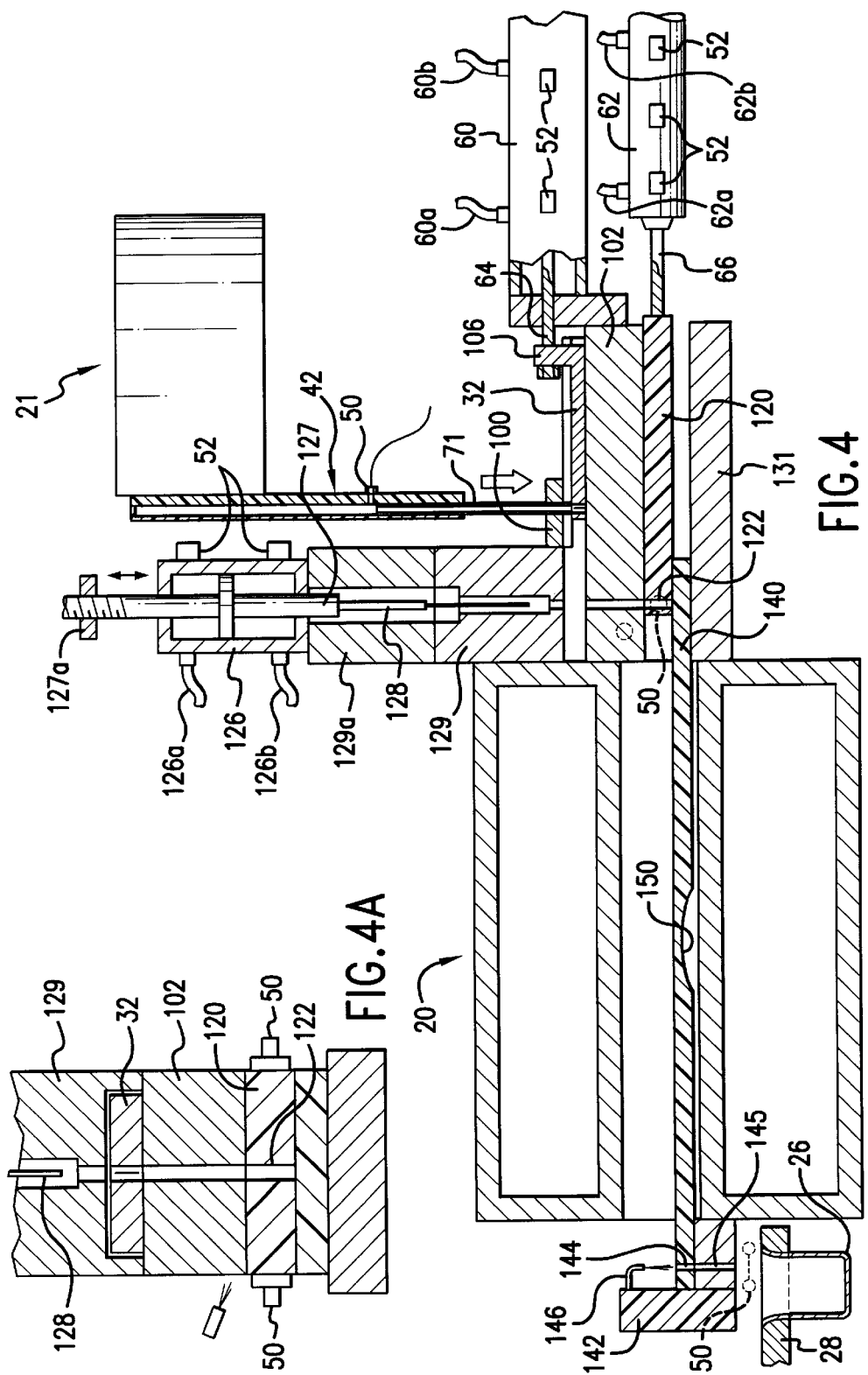

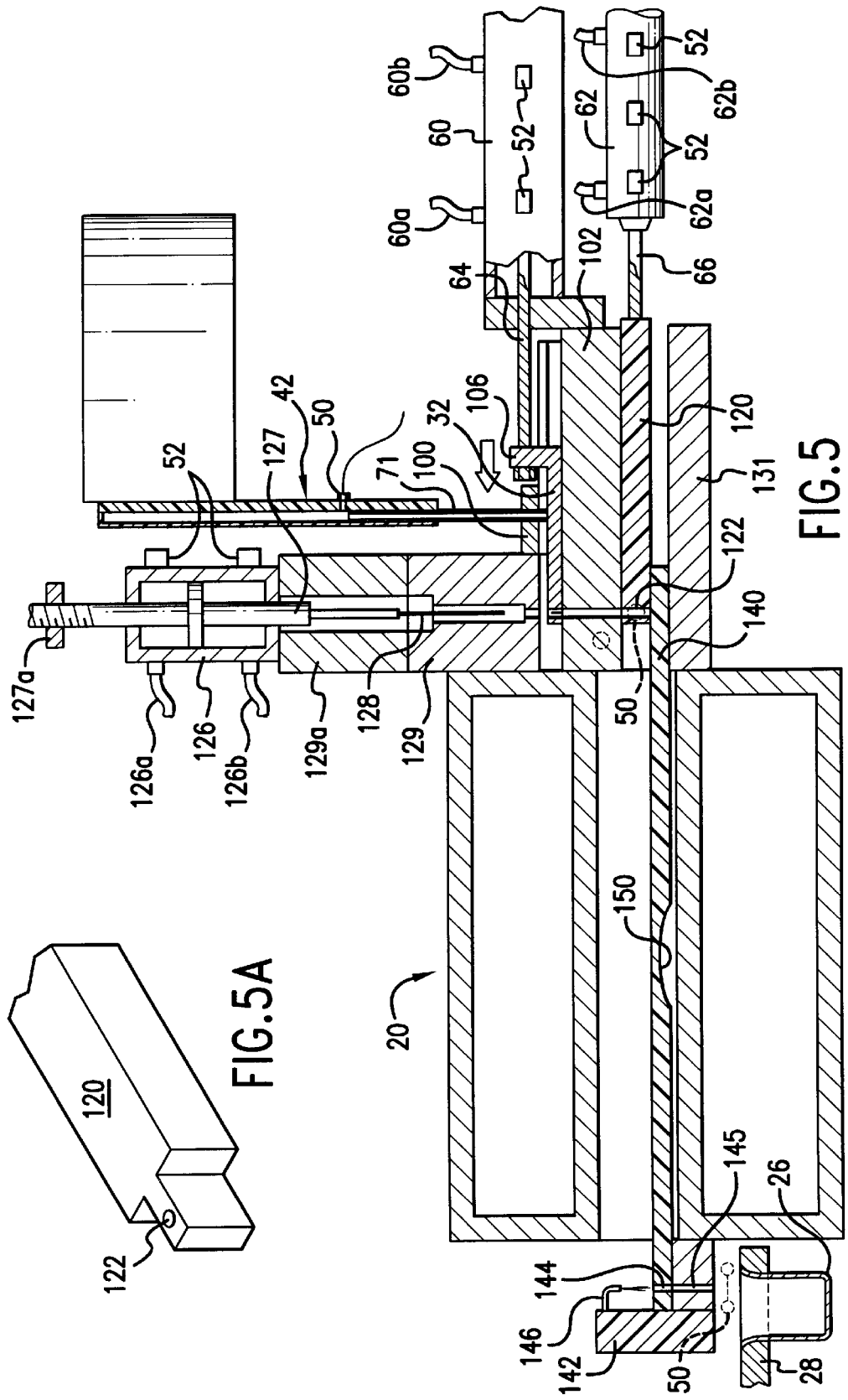

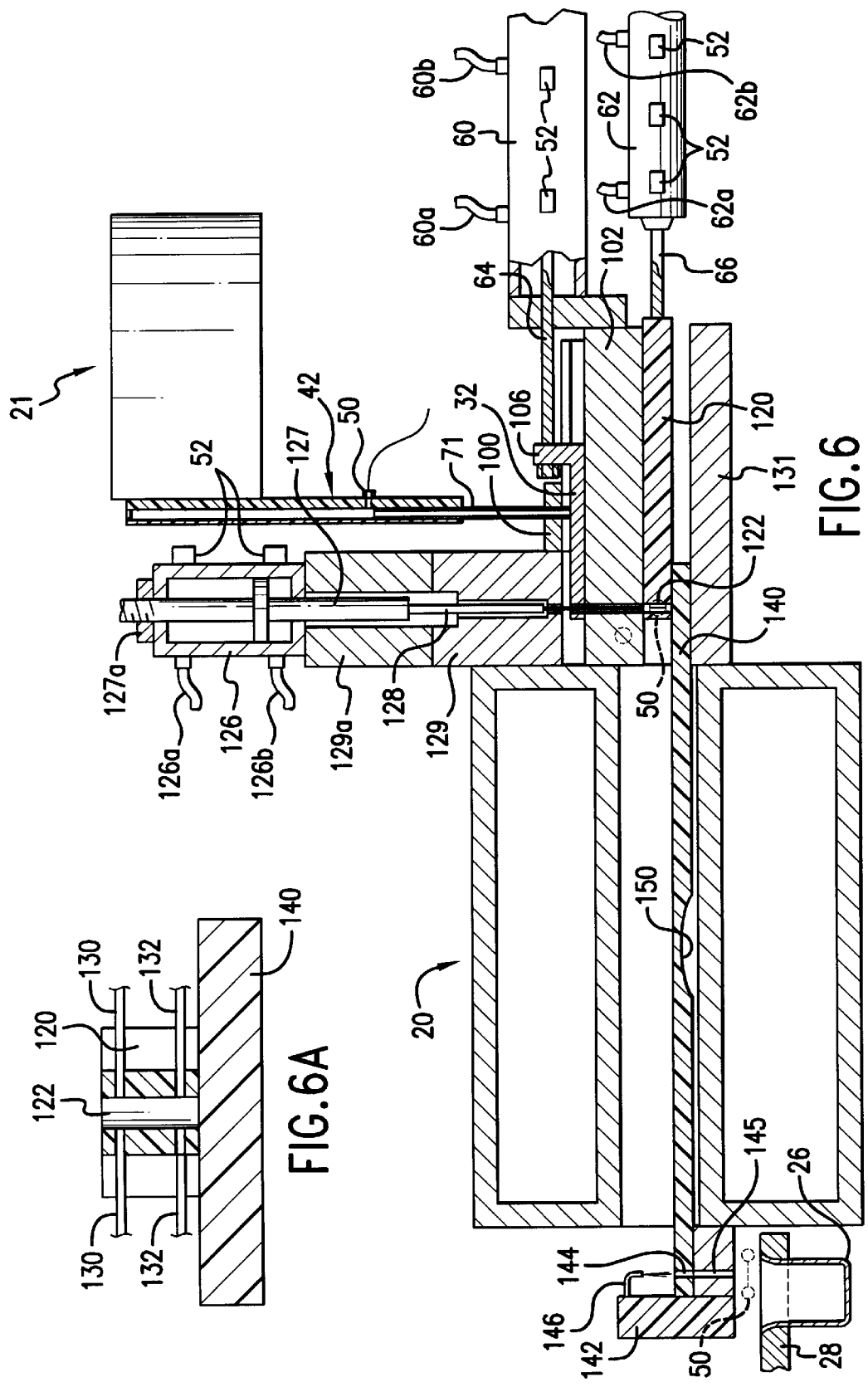

FIG. 18C

COUNT DATA

SEED VALUE 0.034 mCi

PIG 2

| PIG | ACTIVITY LOW LIMIT | SEED COUNT |
|---|---|---|
| 1 | UNDER | 3173 |
| 2 | 0.018 | 1577 |
| 3 | 0.036 | 689 |
| 4 | 0.050 | 230 |
| 5 | 0.055 | 8 |
| 6 | 0.060 | 0 |
| 7 | 0.065 | 0 |
| 8 | 0.068 | 0 |
| 9 | 0.070 | 0 |
| 10 | 0.075 | 0 |
| 11 | 0.080 | 0 |
| 12 | 0.085 | 0 |
| 13 | 0.090 | 0 |
| 14 | 0.095 | 0 |
| 15 | 0.100 | 0 |
| 16 | 0.105 | 6 |
| 17 | 0.110 | 0 |
| TOTAL | | 5683 |

END BATCH

ACTIVE PROGRAM
1

| MAIN SCREEN | COUNT SCREEN | DATA SCREEN | VIEW DATAFILE | FILL TRACK | AIR ASSIST BOWL | AIR ASSIST TRACK | HOME SORT TABLE |

RADIOACTIVE SEED SORTER AND METHOD FOR SORTING RADIOACTIVE SEEDS

BACKGROUND OF THE INVENTION

1. Field of the Invention

The present invention relates to a novel radioactive seed sorter and method for sorting radioactive seeds as used primarily in the medical field.

2. Prior Art

Various seed sorting apparatus has been advanced for the purpose of sorting radioactive seeds as used primarily in the medical field. However, such apparatuses as have been advanced, are particularly cumbersome and do not sort the seeds effectively into a number of dose categories in an efficacious manner. Therefore, a need still exists in the art to provide an apparatus and method that works more effectively and efficaciously to this end.

SUMMARY OF THE INVENTION

The object and purpose of the present invention is to provide an apparatus and method for sorting radioactive seeds into a number of dose categories in a more efficient and efficacious manner than has heretofore been proposed. This is accomplished by the present invention by providing an apparatus and method that utilizes a dose calibrator with special flow-through ionization chamber, a vibratory feeder bowl for feeding radioactive seeds, a mechanical system to singulate, arrange the fed seeds serially one at a time in end-to-end juxtaposition, and to transport the seeds from the feeder bowl through the dose calibrator, and deposit the seed into an appropriate pig in a sorting table. The sorting table (turret wheel) is positioned to present the proper pig to receive the seed, based on its activity. Electronic detectors are provided at particular locations to monitor the transport of seeds through the system, and to position the moving components of the system, and to provide operator safety, and limited containment.

The present invention concerns apparatus for assaying and sorting radioactive seeds comprising a seed feeder having an outlet to feed seeds out the outlet in line horizontally in end to end fashion; a curved track having a horizontal inlet coupled to the outlet of the seed feeder and having a vertical outlet so seeds can drop by gravity out the vertical outlet; an escapement slide having a first cavity to receive a seed positioned below the vertical outlet of the curved track, the escapement slide reciprocating between a first position where the first cavity is in vertical alignment with the vertical outlet of the curved track and a second position where the slide has been shifted horizontally; a shuttle loader located at the second position of the slide comprised of a vertically oriented loader pin arranged for reciprocating vertical movement between a retracted position and a loading position, with the loader pin in vertical alignment with the first cavity of the slide when it is in the second position; a shuttle located below the slide and arranged to move horizontally from a first retracted position, to an intermediate position and to an unloader position, the shuttle having a second cavity that is in vertical alignment with the loader pin when the shuttle is in the first retracted position; a dose calibrator in alignment horizontally with the shuttle to receive the shuttle in its intermediate position and determine the activity of a seed contained in the second cavity, and to allow the shuttle to pass through when moved to the unloader position; a bridge supporting the shuttle and extending from the first retracted position to the unloader position and defining a hole that is vertically aligned with the shuttle second cavity when the shuttle is in the unloader position to allow a seed in the shuttle to drop through the hole by gravity; a sort table having a series of concentrically mounted receptacles, the sort table capable of being positioned with any one of the receptacles vertically below the hole in the bridge to receive a seed dropping through the hole by gravity; and a processor coupled to the dose calibrator and sort table to process the activity determined by the dose calibrator and to instruct the sort table to position a preselected receptacle beneath the hole in the bridge to receive the seed whose activity was determined.

In addition, the invention can have one or more of the following features. The apparatus for assaying and sorting radioactive seeds includes the curved track having a vertical terminal portion and a sensor is associated with the curved track to determine the presence of seeds to a predetermined level in the vertical terminal portion of the curved track. Also, a sensor is associated with each of the first cavity and second cavity, each sensor determining the presence of a seed respectively associated cavity. Piston-cylinder assemblies are provided coupled to drive the slide and shuttle. Sensors are associated with the piston-cylinder assemblies to control the actuation thereof. The bridge has a cutout at the location corresponding to the intermediate position of the shuttle. The dose calibrator is of annular configuration. The feeder includes a track leading to the feeder outlet with the track having a cutout adjacent to the outlet and an air assist is provided to cooperate with the feeder in the vicinity of the outlet to maintain seeds in a single line. An air assist is provided to cooperate with the curved track. An air jet is positioned over the hole defined in the bridge.

Still further, the invention provides a method for assaying and sorting radioactive seeds comprising the steps of: feeding seeds in line horizontally in end to end fashion; translating the seeds from the horizontal to a vertical stack; singulating the seeds from the vertical stack and moving a singulated seed to a horizontally displaced position; loading the horizontally displaced singulated seed into a shuttle by pushing vertically downward into a cavity in the shuttle; moving the shuttle horizontally from a retracted position where it receives a singulated seed, into one end of an annular dose calibrator to an intermediate position within the dose calibrator and out of the other end of the annular dose calibrator to an unloader position; determining the activity of the singulated seed contained in the cavity while it is in the intermediate position; dropping the singulated seed into one of a plurality of receptacles at the unloader position; and controlling the plurality of receptacles to position a preselected receptacle to receive the singulated seed based on the activity determined.

The method for assaying and sorting radioactive seeds according to the invention can include the further step of sensing the presence of seeds in the vertical stack; the further steps of sensing a seed when initially singulated and sensing a singulated seed in the shuttle; the steps of driving the initially singulated seed to the horizontally displaced position and driving the shuttle between its positions; the further step of controlling the driving of the initially singulated seed and shuttle; the further step of supporting the shuttle at the intermediate position with a reduced section; the step of blowing air into the seeds during translation from the horizontal to the vertical; the further step of blowing air at the seeds to assist in maintaining the horizontal in line feeding of seeds; the further step of blowing air toward the singulated seed to assist in the step of dropping the singulated seed into a receptacle; and the further step of sensing the dropping of a singulated seed into a receptacle.

Other and further objects and advantages of the invention will become more readily apparent from the following detailed description of a preferred embodiment of the invention when taken in conjunction with the appended drawings.

BRIEF DESCRIPTION OF THE DRAWINGS

FIG. 1B is a perspective view of the apparatus showing the Lexan protective cover;

FIG. 4 is a side view, partly in section, of the apparatus showing loading of the escapement;

FIG. 4A is a view in section showing a detail of the escapement mechanism;

FIG. 5 is a side view, partly in section, like FIG. 4, of the apparatus showing the escapement mechanism shifted into position for shuttle loading;

FIG. 5A is a perspective view of the shuttle;

FIG. 6 is a side view, partly in section, showing the loading of the seed into the shuttle;

FIG. 6A is a view in section showing the seed holder cavity of the shuttle;

FIGS. 18a, 18b and 18c are schematic representations of the display screen of the computer.

DETAILED DESCRIPTION OF PREFERRED EMBODIMENTS OF THE INVENTION

Figure 1:
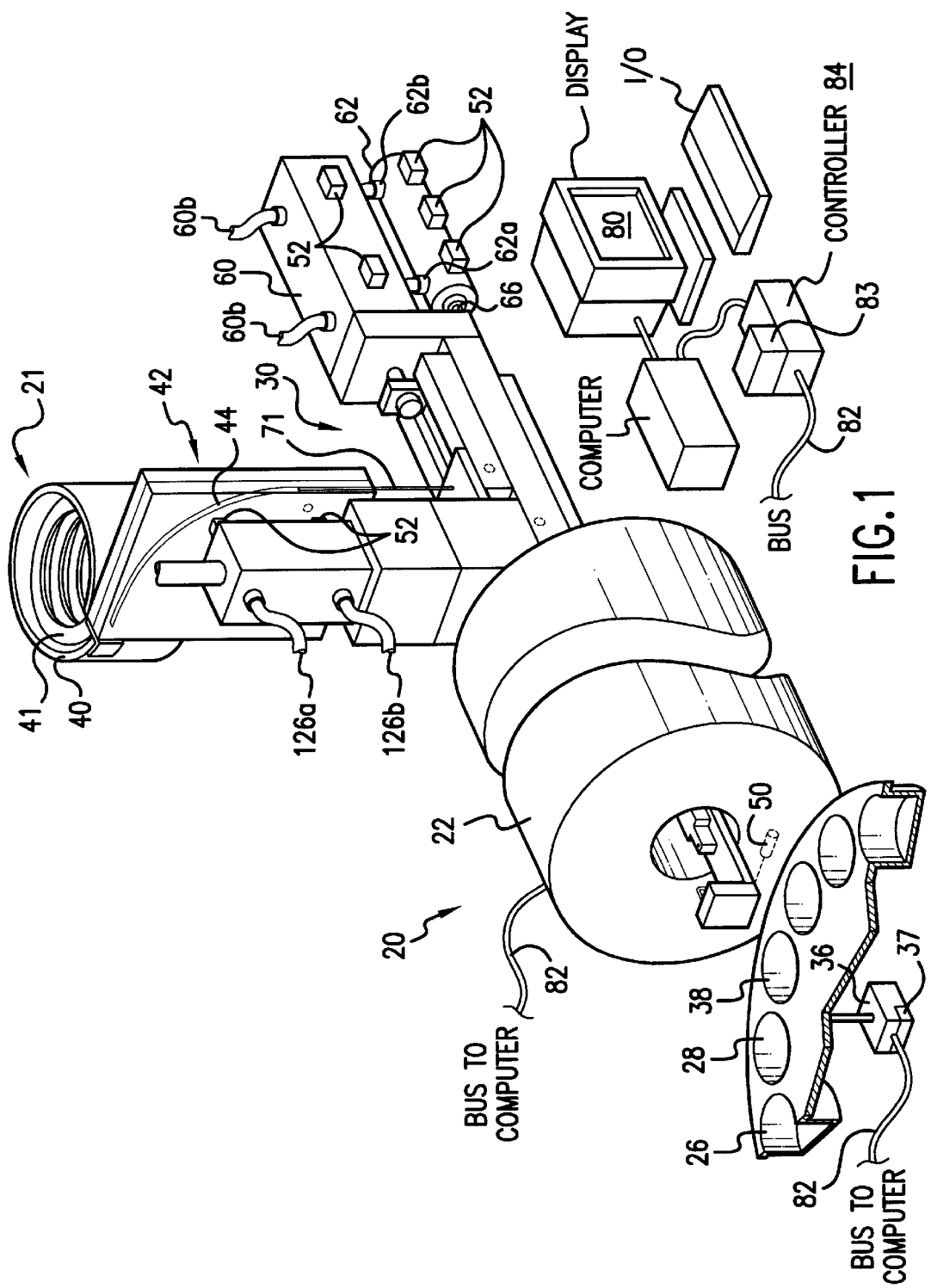
FIG. 1 is a perspective view of the novel apparatus.

The present invention will now be described with respect to a preferred embodiment to enable a person of ordinary skill in the art to make and use the present invention. However, the description of a preferred embodiment shall not constitute a limitation on the scope or content of the invention, as changes and modifications of the preferred embodiment can be made, as will be apparent to those of ordinary skill in the art, from the teachings of the invention as embodied in the preferred example herein described.

Referring now to the FIGS. 1 to 8 the drawing, the apparatus of the invention consists of an annular dose calibrator generally designated as 20 with special flow-through ionization chamber 22. For this purpose, a Capintec CRC-127® dose calibrator, made and sold by Capintec, Inc. of Ramsey, N.J., can be used, as an example. The Capintec CRC-127® dose calibrator 20 is provided with a special flow-through annular ionization chamber 22. In addition to the above, a vibratory feeder system 21 is provided into which the seeds to be sorted are initially placed, including a bowl 40 and an exit (inline) track 41. The inline exit track 41 is coupled directly to a mechanical system to singulate the seeds from the feeder bowl 40 via a curved track 44 into an escapement 30, and then, through the dose calibrator 20, and deposit the seeds into appropriate pigs 26 in a sorting table 28 according to there dose measurements. The escapement 30 is a mechanism that inserts one seed into the system at a time for processing. As will be explained in more detail hereinafter, the escapement 30 consists of a DELRIN slide 32 and housing 34 mounted at the end of the feeder exit track. DELRIN is an acetal resin (DuPont registered trademark), which is a highly versatile engineering plastic with metal-like properties. It provides high tensile strength, impact resistance, and stiffness, as well as, fatigue endurance, dimensional stability, resilience and resistance to creep and natural lubricity. The seeds are radioactive and are elongated rods having rounded ends.

A sorting table (turret wheel) 28 including a motor 36 positions the proper pig 26 to receive the seed, based on its activity, as determined by the dose calibrator 20. Sort table 28 consists of an aluminum wheel, or turret 38 with room for 17 concentrically placed stainless steel pigs 26.

A computer 80 containing a microprocessor controls the operation of the system, as will be explained in more detail hereinafter. Pneumatic cylinders 60, 62, devices consisting of cylinders with pistons, in combination with projecting piston rods 64, 66, are employed to translate or shift the seeds from one position to another through the apparatus and in the system. The cylinders 60, 62 are arranged with controls that use magnetic Hall effect sensors 52 to provide precise position status to the computer, which, in turn, controls the actuation of the cylinders. The Hall effect sensors 52 are magnetic sensors that are employed to monitor the position of the cylinders for control input. 2 and 3 position cylinders are used in the seed sorter apparatus and system, as will be described in more detail hereinafter.

Electronic detectors, including the Hall effect sensors 52 and photosensors 50, optical sensors, are used to verify the presence or absence of a seed, and to ensure it is properly positioned, and to monitor the transport of seeds through the system, and the position of moving components.

Figure 1A:
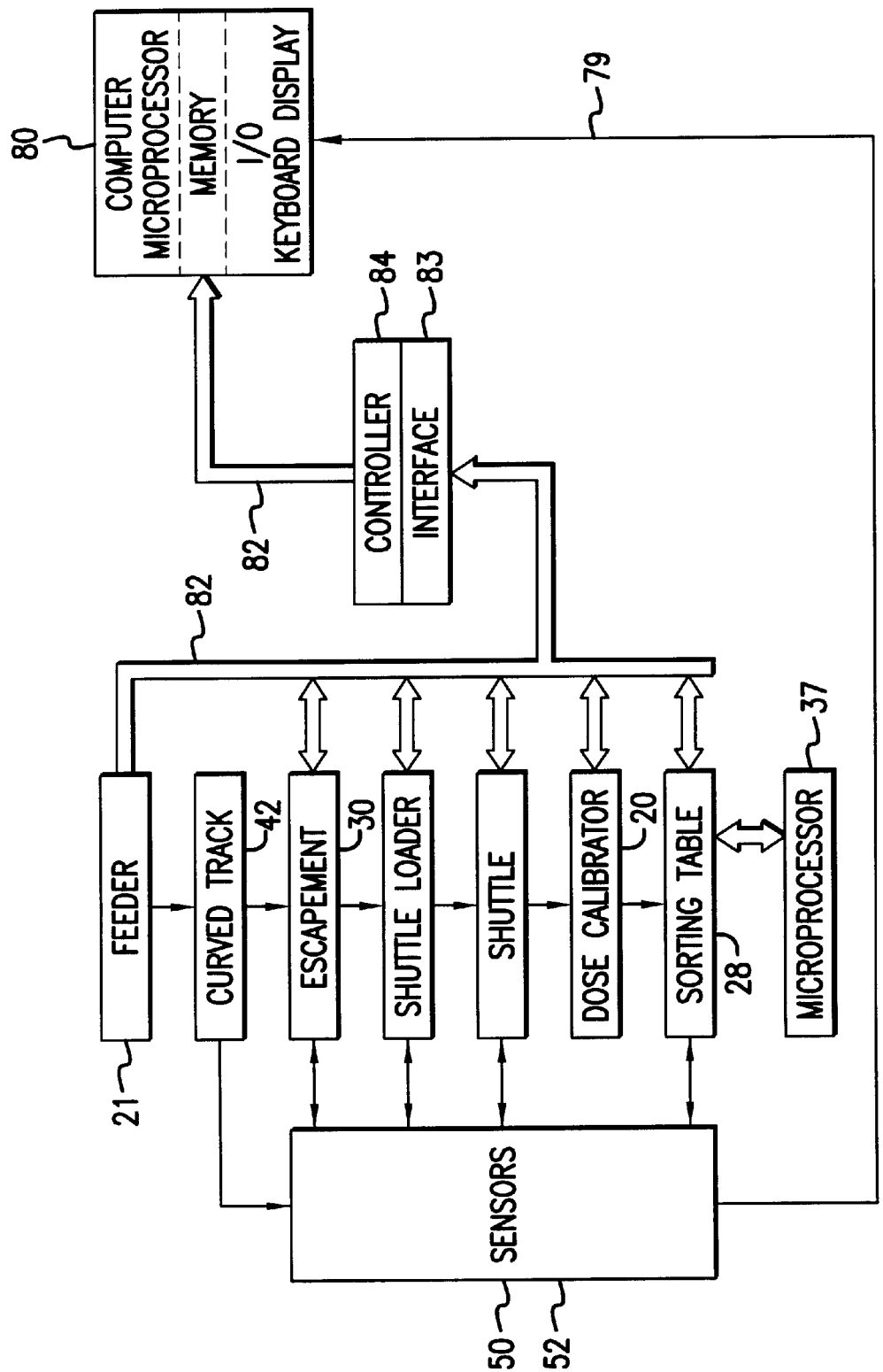
FIG. 1a is a block diagram of the novel apparatus shown in FIG. 1.
Figure 2:
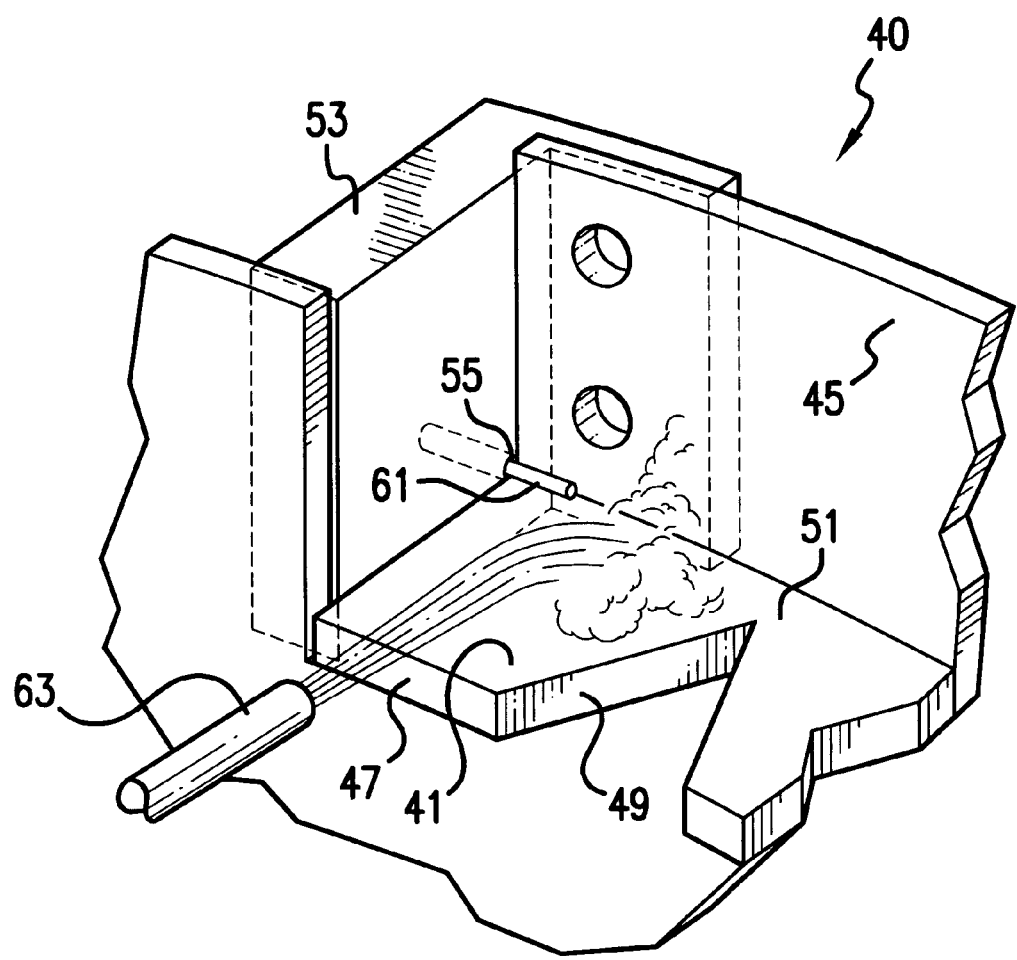
FIG. 2 is a perspective view of a detail showing the initial singulation of the seeds.

A LEXAN enclosure 70, see FIG. 1b, serves to provide operator safety, and limited containment. LEXAN is a transparent polycarbonate plastic (GE's registered trademark), which is difficult to break due to its elasticity and flexibility. A table 72 with stainless steel top is provided on which the system is mounted. The sort table motor 36 has an embedded microprocessor 37 that contains a small program to optimally control position, velocity, acceleration, and direction of travel. Communications from computer 80 (including a microprocessor, memory, I/O such as a keyboard and display) with the dose calibrator 20 and sort table motor 36 are implemented over an RS-232 interface 83, with a standard Interbus RS-232 interface controller 84. Bus 82 interconnects the computer 80 with system components, and sensors 50, 52 are connected to provide inputs to computer 80, as shown in FIG. 1a, via line 79.

As noted, the apparatus consists of a vibratory feeder bowl 40, a mechanical system comprised of curved track device 42 and escapement 30 and a shuttle loader to singulate and transport the seed from the feeder bowl 40 through the dose calibrator 20, and deposit the seed into an appropriate pig 26 in a sorting table 28. The sorting table 28 is an aluminum wheel, or turret 38 with room for 17 concentrically placed, peripherally spaced stainless steel pigs 26. The sorting table 28 (turret wheel) is motor driven to position the proper pig to receive the seed being assayed, based on its activity. Electronic detectors (both photosensors 50 and magnetic Hall effect sensors 52) monitor the transport of seeds through the system, and the position of moving components. The photosensors 50 comprise optical sensors used to verify the presence or absence of a seed, and to ensure it is properly positioned. Hall effect sensors 52 are magnetic sensors employed to monitor the position of the cylinders for control input. The cylinders 60, 62 are pneumatic devices that, in combination with piston rods 64, 66, are employed to translate or shift the seed from one position to another. All cylinders have magnetic Hall effect sensors to provide precise position status to the computer. 2 and 3 position cylinders are used in the seed sorter.

The LEXAN enclosure 70 serves to provide an operator of the apparatus safety, and limited containment. LEXAN is a registered trademark of the General Electric Company and consists of a transparent polycarbonate plastic, which is difficult to break due to its elasticity and flexibility. The system is mounted on a table 72 with stainless steel top. The sort table motor 36 has an embedded microprocessor 37 that contains a small program to optimally control position, velocity, acceleration, and direction of travel. Communications with the dose calibrator and sort table motor are implemented over an RS-232 interface, with Interbus RS-232 interface controller and a standard PC computer.

The mechanical system to singulate the radioactive seeds, as shown in detail in FIGS. 1–8 consists of a known vibratory feeder system 21, modified as described below, into which the seeds are initially placed, including a bowl 40 and an exit (inline) track 41. The bowl 40 of the vibratory feeder is a 3 inch bowl that sits on a pedestal 43 at the front of the system. A batch of seeds is placed in the vibratory feeder bowl 40. During operation and due to vibration, the seeds follow a spiral track 41 up the bowl 40. The track has a width greater than the thickness of the seeds, and thus, a plurality of seeds may reside laterally on the track from the outermost portion adjacent the guide wall 45 forming the outer boundary of the track and its inner free edge 47. There is a notch 49 in the track 41, located spaced from the end of the track, that extends from the inner free edge 47 of the track toward the outermost portion 45 of the track and terminates short of the outermost portion 45, as indicated by reference numeral 51, to enable seeds at the outermost portion to pass by the notch 49. This notch 49 provides back-pressure relief by passing only the lateral-outermost seed 61, as noted, while forcing the other seeds on the track 41 passing inwardly, to fall back into the bowl 40. An L-shaped termination piece 53 is bolted to the top end of the track. The termination piece 53 presents a small in-line opening 55 with the outermost portion of the top of the spiral track 41 and has a nose piece 57 on its outside that is characterized by an extending tube (outlet) that is inserted in curved track 44 to enable delivery of the seeds (horizontally in line end-to-end) being fed by the vibratory feeder directly into the entrance of curved track 44 and thereby begin the translation from horizontally fed seeds into a single file (end-to-end) of vertically fed seeds.

The curved track device 42 is comprised of LEXAN so that it is transparent, and track 44 of device 42 carries the seeds from the feeder bowl output to the escapement 30. It transfers the seeds from a horizontal orientation at the beginning of the track 44, to a vertical orientation at the end, a vertical stack of seeds. A pre-escapement photosensor 50, near but spaced vertically from the bottom of the track 44, detects if the track 44 is full to this level (stack reaches this level), and shuts the feeder bowl off. When 10 seeds have been processed after shut off, the feeder 21 is turned on again until enough seeds have been loaded to once again block the sensor 50. The curved track 44 ends at a vertical hypodermic tube 71 that feeds seeds into the escapement 30.

Two air assists 63 and 65 are positioned at the beginning of the curved track 44. The feeder bowl air assist 63 ensures that seeds at an angle to the nose piece 57 do not block the passage 55. It is activated periodically when seeds are being loaded into the curved track 44. The track air assist 65 provides an additional push down the curved track 44 so that seeds which may not have sufficient back pressure move forward. Both can be manually activated from the control bar at the bottom of the screen display on the computer 80 as seen in FIG.18.

The curved track device 42 carries the seeds from the feeder bowl 40 output in a horizontal orientation to an escapement 30 where the seeds are lined up end-to-end in a vertical orientation. The escapement 30 is a mechanism that inserts one seed into the system at a time for processing. The escapement consists of a DELRIN slide 32 and housing 34 mounted at the end of the feeder exit track (the end of the hypodermic tube 71. As previously noted, DELRIN is a registered trademark of the E. I. du Pont Company and consists of an acetal resin that is a highly versatile engineering plastic with metal-like properties that provides high tensile strength, impact resistance, and stiffness, fatigue endurance, dimensional stability, resilience and resistance to creep and natural lubricity. The curved track 44 transfers the seeds from a horizontal orientation at the beginning of the track, to a vertical orientation at the end. A pre-escapement photosensor 50, near the bottom of the track, detects if the track is full to that level, and shuts the feeder bowl 40 off. When 10 seeds have been processed, the feeder 40 is turned on again until enough seeds have been loaded to once again block the sensor 50. The curved track 44 ends in a vertical hypodermic tube 71 that feeds seeds, one at a time, into the escapement 30.

As noted, two air assists 63, 65 are positioned at the beginning of the curved track device 42, one 63 in the feeder bowl 40 and one 65 feeding air into the curved track 44. The feeder bowl air assist 63 ensures that seeds at an angle to the nose piece 57 do not block the passage 55. It is activated periodically when seeds are being loaded into the curved track. The track air assist 65 provides an additional push down the curved track so that seeds which may not have sufficient back pressure move forward. Both can be manually activated from the control bar at the bottom of the computer screen.

The escapement 30 consists of housing 34 formed of a top brass block 100, a bottom brass plate 102 on which slide 32 slides, and a pair of side gibs or guides 104. The slide 32, which has a vertical hole or cavity 108, see FIG. 3a, for receiving a seed, rides on plate 102 and is guided by the gibs 104 for linear reciprocation between a loading position #1 and an unloader position #2 where a seed will be transferred to a shuttle. An L-bar 106 connects the slide 32 to piston rod 64 of cylinder 60 with which is associated Hall effect sensors 52 to delineate the two positions. Air from a compressed source is admitted and exhausted from the cylinder 60 via fittings 60a and 60b. In position #1, the hole 108 is vertically aligned with the end of hypodermic tube 71, which is held fixed in block 100. In this position, the slide 32 receives a seed, by gravity feed, from the end of tube 71. A photosensor 50, see FIG. 3b, assures, via a through optical path that a seed is in hole or cavity 108.

The purpose of the escapement 30 is to singulate a seed from those behind it. A seed is advanced into the escapement cavity 108 from the vertical hypodermic tube 71 providing a termination for the curved track 44. As noted above, the escapement cavity 108 is in a DELRIN escapement slide 32. The slide 32 is held in place by a brass block 102 behind (beneath) it, with upper and lower gibs 104 which guide the slide 32 for horizontal reciprocating movement. The escapement slide 32 is driven by the piston rod 64 of pneumatic cylinder 60 which advances it from the escapement loading position (retracted), position #1, where the seed is loaded into the escapement slide, to the seed holder unloading position (inserted), position #2, where the seed is transferred or loaded into a shuttle 120 for movement through the dose calibrator 20.

To ensure the seed is completely inserted into the cavity, the escapement photosensor 50 is employed to indicate that the seed is within a predetermined dimension, e.g., less than 0.003 inch of the back of escapement cavity 108.

If the seed in the cavity 108 is at the lower limit of the specified length, the seed behind it may be partially inserted into the cavity 108. There is an exclusion ramp 110 behind the cavity 108 on the escapement slide 32 to ensure the next seed is pushed back as the slide 32 advances to position #2, see FIG. 3a.

Figure 3:
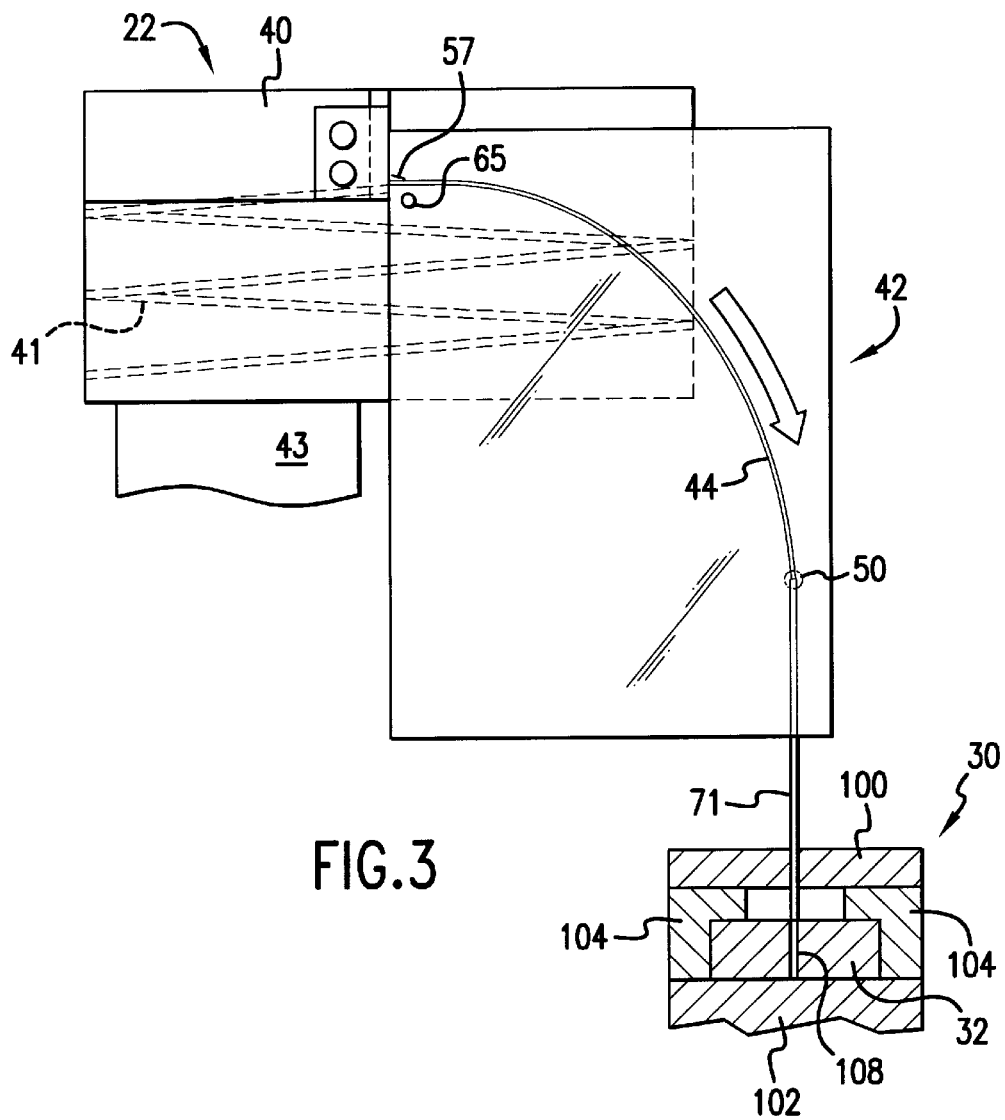
FIG. 3 is a side view of the singulation of the seeds.
Figure 3A:
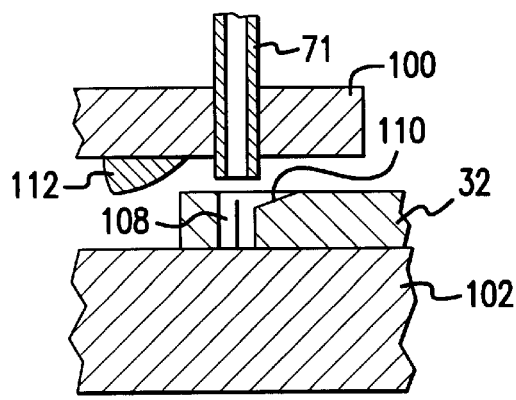
FIG. 3a is a detail view of the escapement showing ramps.
Figure 3B:
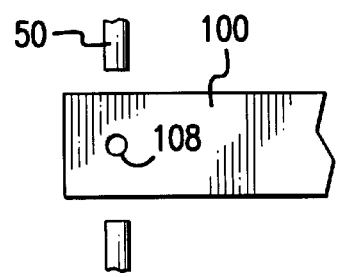
FIG. 3b is a top view of the escapement slide showing a photosensor arrangement.
Figure 7:
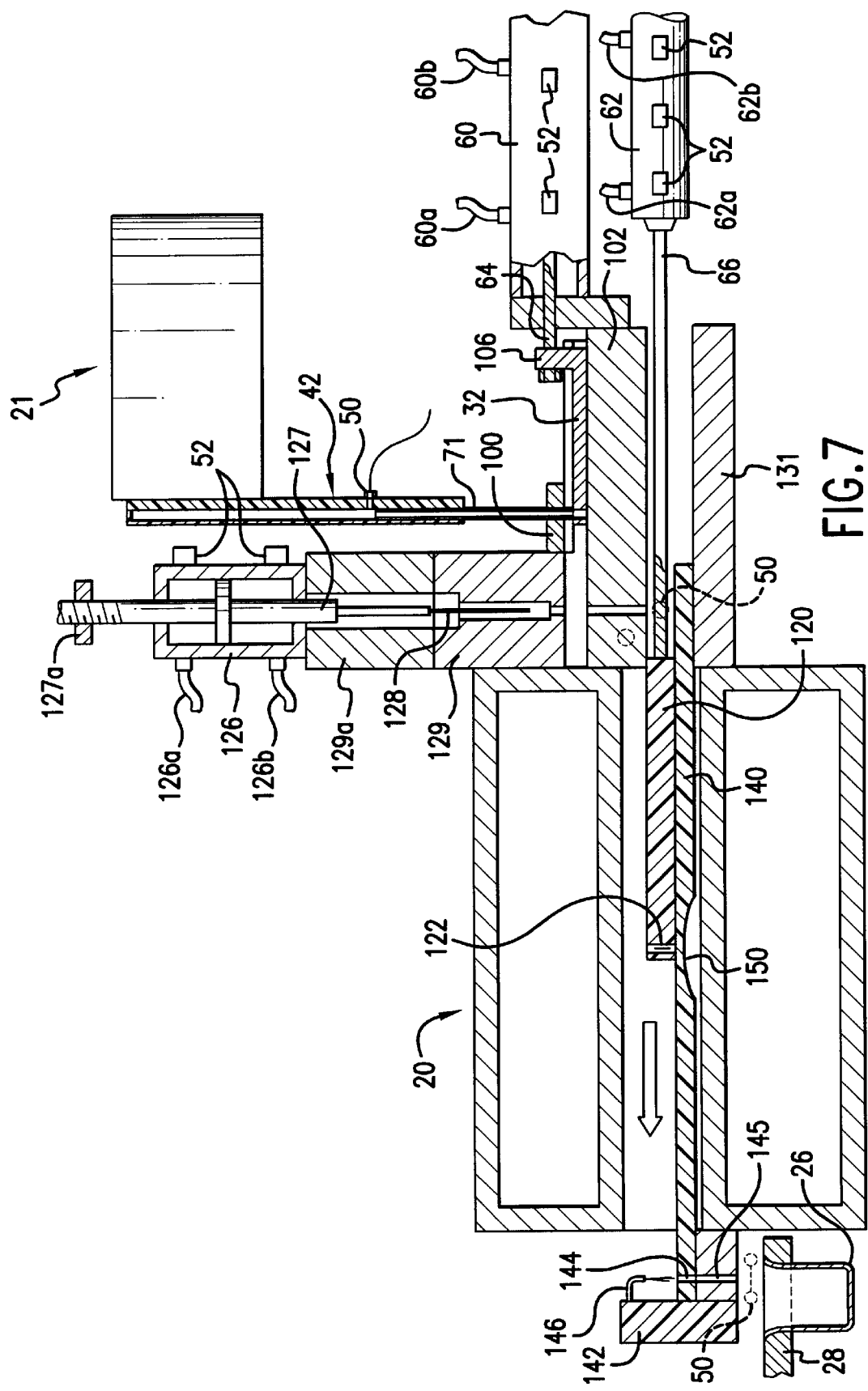
FIG. 7 is a side view, partly in section, showing the shuttle shifted into the ionization chamber to a midpoint thereof where measurement takes place.
Figure 8:
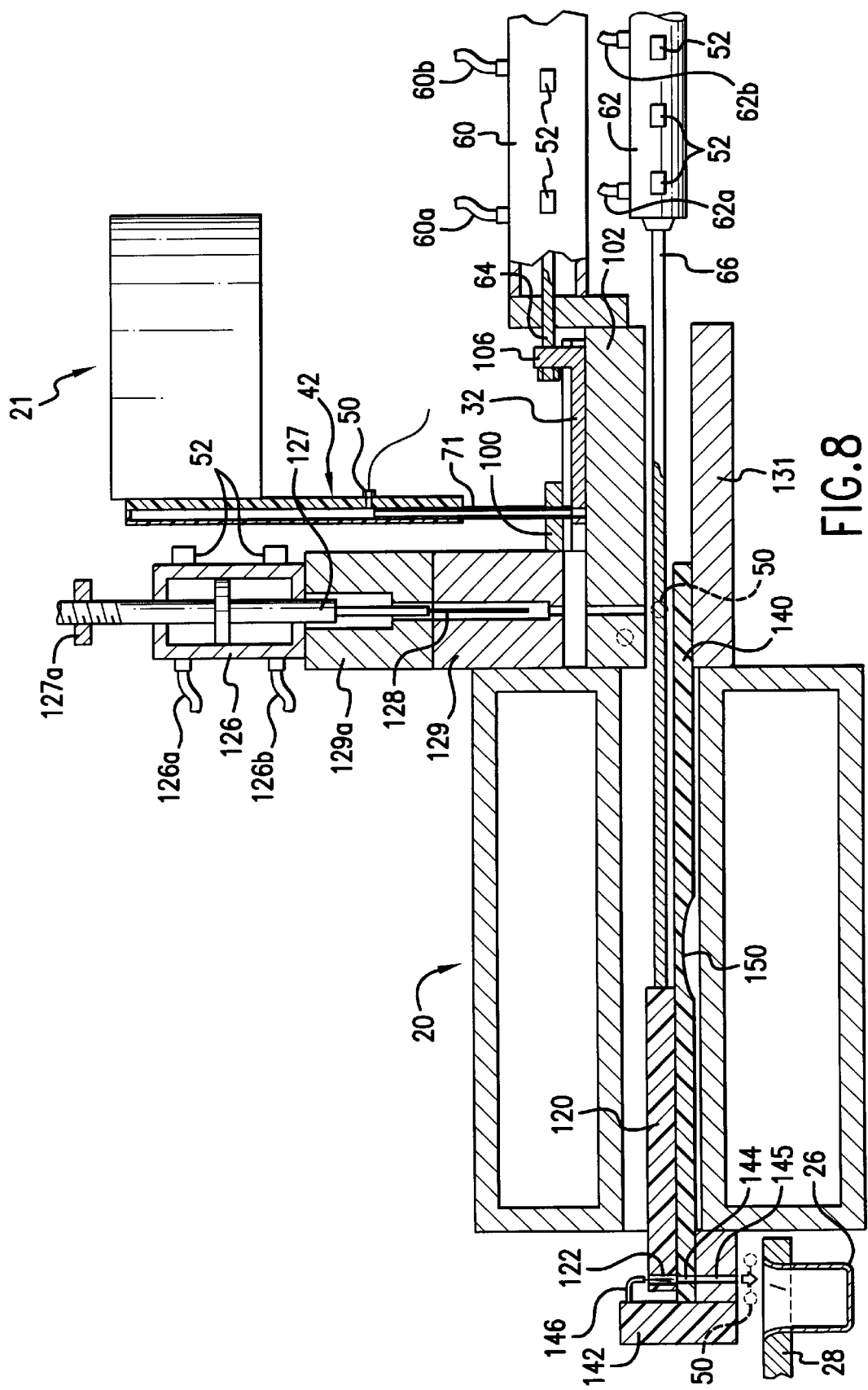
FIG. 8 is a side view, partly in section, showing the shuttle shifted to the outside of the ionization chamber to the position where the seed is dropped into the appropriate pig.

If, within the cavity 108, the end of the seed facing the vibratory track 44 is protruding slightly from the escapement cavity 108, an insertion ramp 112 on the lower surface of block 100 adjacent to the escapement slide 32 will push the seed completely into the cavity 108 as the slide 32 advances passed the ramp 112, see FIG. 3a.

The seed shuttle 120 is a second DELRIN slide used to hold the seed as it is inserted in the dose calibrator 20 for activity assay, and advanced to the position where the seed is deposited into the correct pig 26. When inserted into the seed shuttle 120, which serves as the seed holder, the seed is contained in a cavity 122 at the end of a narrow ¼" rod extension 124 of the shuttle 120, see FIG. 5a. The seed holder 120 is advanced by 3 position pneumatic cylinder 62 and piston rod 66 connected to the end of the shuttle 120 under the control of the Hall effect sensors 52. Air from a compressed source is admitted and exhausted from the cylinder 62 via fittings 62a and 62b.

In the retracted (inserted) position A, a seed is loaded into the shuttle holder 120, see also FIGS. 9–14, which show the sequences. In this position, the slide 32 is in position #2. A pneumatic cylinder 126 via a piston rod 127 with a piston fixed thereto drives a loader pin 128 fixed to the end of the piston rod 127 guided by a brass block 129 and a spacer block 129a, to push the seed from the escapement cavity 108, in the inserted position A, through brass block 102 into the cavity 122 of the shuttle 120 seed holder. Air from a compressed source, admitted and exhausted via fittings 126a and 126b, drives the cylinder 126, and Hall effect sensors 52 govern its stroke. The end of pin 128 is chamfered at 45 degrees to minimize wear on the seed cavity. The chamfer does not affect applied pressure to the seed, since the end of the seed is rounded, so the contact point between the pin and seed is a fairly small point in the center of the face of the pin.

A photosensor 50 detects that the seed is properly inserted into seed holder cavity 122. There are two sets of two holes (an upper set 130 and a lower set 132) perpendicular to the seed cavity 122, each set or pair of two holes is horizontally coaxially aligned, see FIG. 6a. The lower pair of holes 132 is the optical path. The upper pair of holes 130 allows air to enter the cavity 122 as the inserter pin 128 is retracted. Because the seed is oriented vertically, a TEFON bridge 140 is used below the shuttle 120 to keep the seed within the shuttle cavity 122. Side guides 141 assist in the reciprocal movement of the shuttle 120. A support plate 131 supports the bridge on both sides of the calibrator 20. As the shuttle 120 is moved by the cylinder 62, it moves from the inserted position A where the seed is loaded into cavity 122, to the a mid-position B of the bridge 140 where the activity of the seed is measured, see FIG. 7, and finally, to the inserted position C where is out of the calibrator 20 and where the seed is dropped into the correct pig 26, see FIG. 8. At the end of the shuttle track, the bridge 140 ends at an upright 142 and the bridge has a vertical hole 144 adjacent the end of the bridge 140. Hole 144 is vertically aligned with the vertical path of the seed, allowing the seed to drop through the hole 144 provided in the bridge 140, through a hole 145 in the support plate 131 and into the cup or pig 26 in the inserted position C.

The bridge 140, in the middle position B of the shuttle 140, is provided with a reduction in thickness by arcuate cutout 150. In this position, the seed is positioned for activity assay in the ionization chamber of the calibrator 20. It is located in the sweet spot, approximately 6 inches from the entrance (side of entry of the shuttle 120). In the inserted position C of the shuttle 120, the seed is unloaded from the shuttle 120 holder, and deposited into the appropriate pig 26. As noted, after assay is complete, a seed is advanced to the seed unloader position C above the sort table 28. The seed shuttle 120 is in the inserted or the unloader position C when the piston rod 66 of the seed shuttle cylinder 62 is fully extended. The inserted or unloader position C is located or positioned above the sort table 28, in line with the center of a pig 26. The seed drops through the guide hole 144 in the bridge 140, through hole 145 in plate 131 and into the appropriate pig 26. An ejector air jet 146 located vertically aligned above hole 144 provides an additional push to clear the shuttle 120 of the seed to be unloaded. As the seed drops, it is detected by a photosensor 50 to ensure that it has left the shuttle 120 holder, and has fallen into the correct pig 26.

The sort table 28 is rotated so that the seed will be deposited into the pig 26 with the correct activity range. This rotation occurs before the advancement of the seed shuttle 120 to the inserted or unloader position C. A stepper motor 36 rotates the sort table 28 under the control of the computer 80. The motor 36 precisely controls acceleration and velocity, and feeds back its absolute position to the computer. The sort table 28 begins rotation as soon as seed activity is known (determined by the dose calibrator 20 and sent to computer 80).

The material handling portion of the apparatus is mounted on a stainless steel tabletop 72 housed in a LEXAN enclosure 70. The enclosure is connected to a vacuum source 150 at the top to provide a constant but small inflow of air through all gaps in the enclosure, thus assisting in the containment of any escaping radioactive material.

The dose calibrator system and activity measurement is effected in the following manner, see FIG. 17. The dose calibrator system includes a CRC 127 dose calibrator readout, a dose calibrator flow-through ionization chamber and serial connection (RS-232) to the Interbus RS-232 controller, as previously noted. The dose calibrator readout is a Capintec model CRC-127, that provides a digital output at an increased sampling rate (approximately 3 times per second, which exceeds the 0.6 second sampling rate of a Control Program). This ensures a new reading each time a reading is requested by the Control Program of computer 80. The flow-through ionization chamber contains the high voltage bias supply within the chamber, which reduces noise and the response time.

Figure 17:
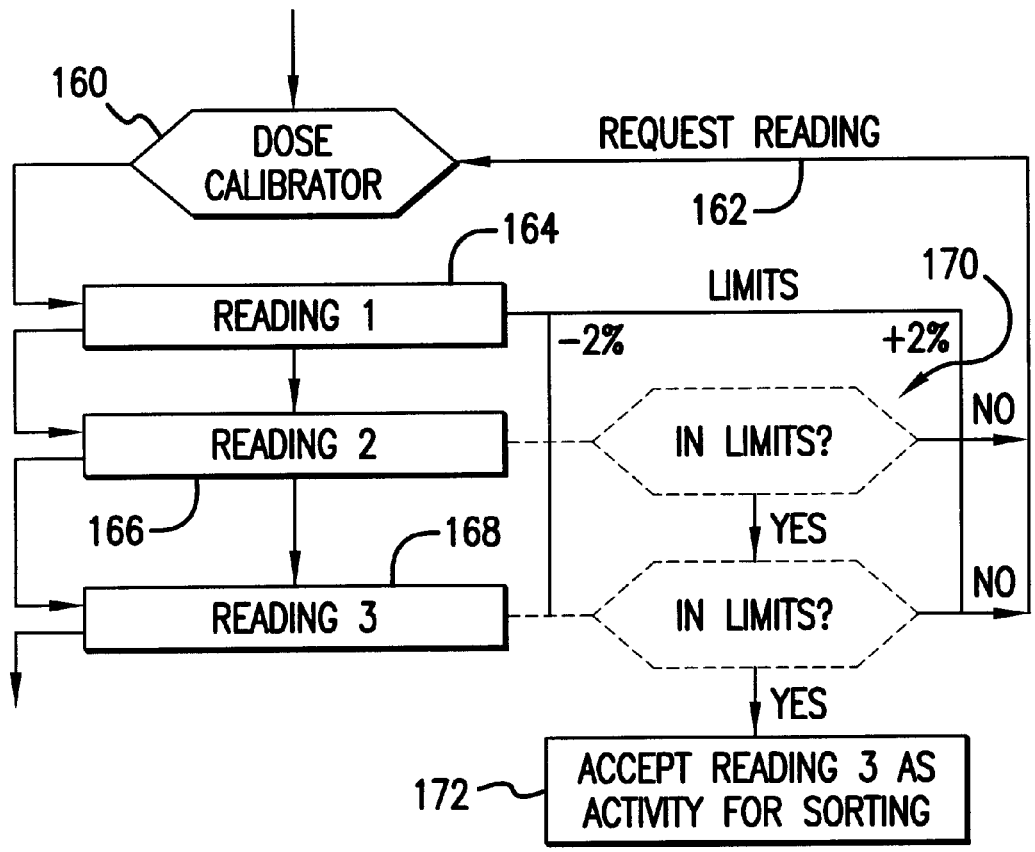
FIG. 17 is a flowchart of the activity measuring algorithm.

The activity measurement algorithm is shown in FIG. 17 and operates as follows. After a seed is positioned in the dose calibrator as shown in block 160 by the mechanical system, the Control Program begins requesting the activity read by the dose calibrator, see input 162. Activity is sampled at a period of 0.6 seconds. The three most recent readings, readings 1, 2 and 3 (164, 166, 168) are stored in a queue. The readings are checked to determine if they are within limits of −2% to +2%, see reference number 170. If the two most recent readings are within 2% of the oldest reading, then the most recent reading 168 is deemed stable and is accepted in block 172 and used for sorting the seed.

Figure 9:
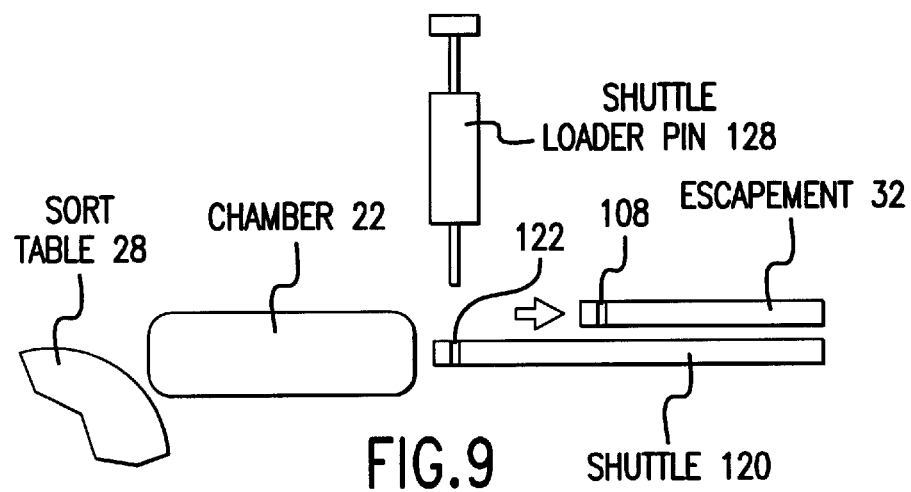
FIGS. 9 to 14 are schematic views showing the sequence of the operational states of the novel apparatus.
Figure 10:
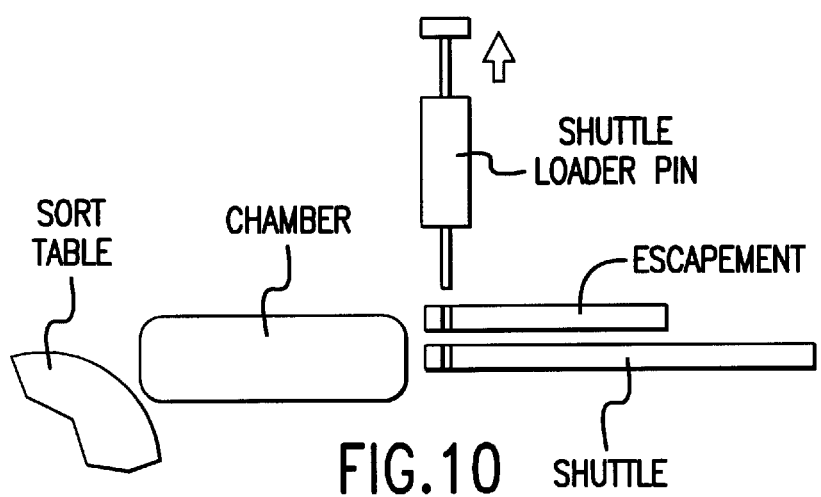
Figure 11:
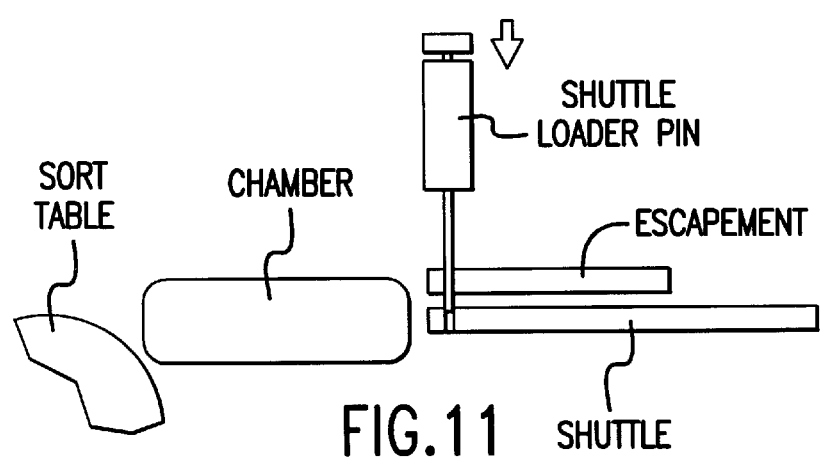
Figure 12:
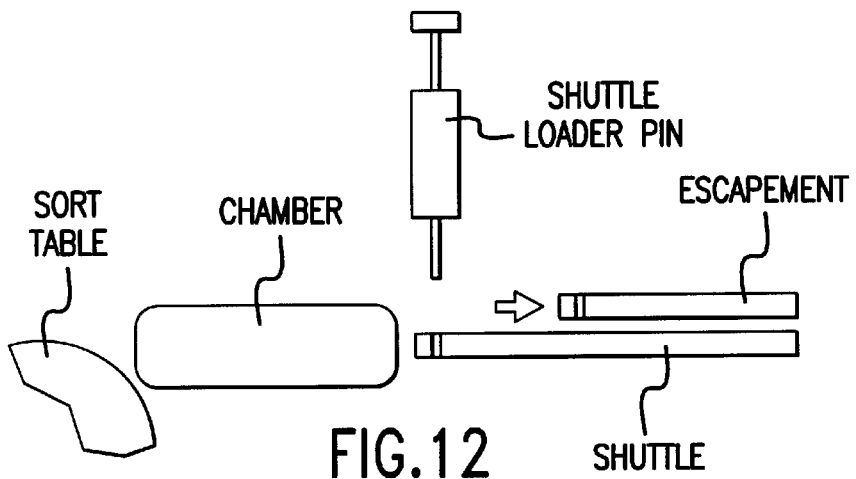
Figure 13:
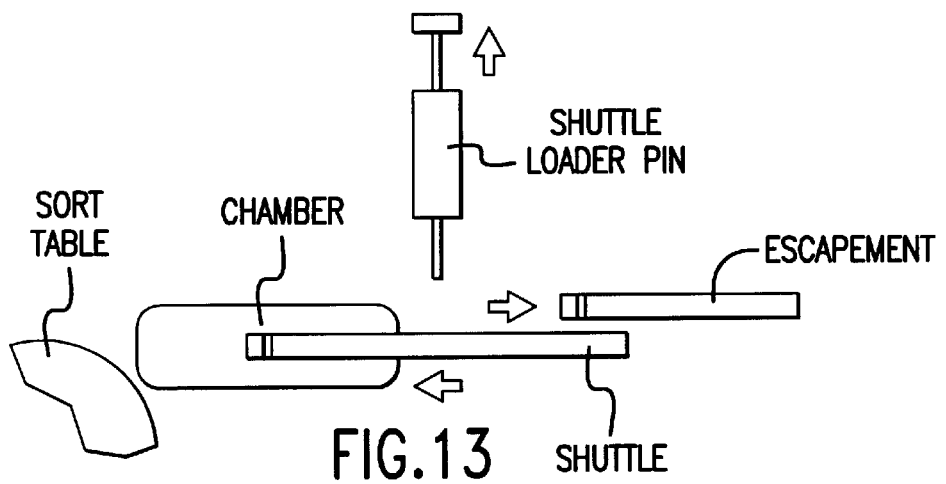
Figure 14:
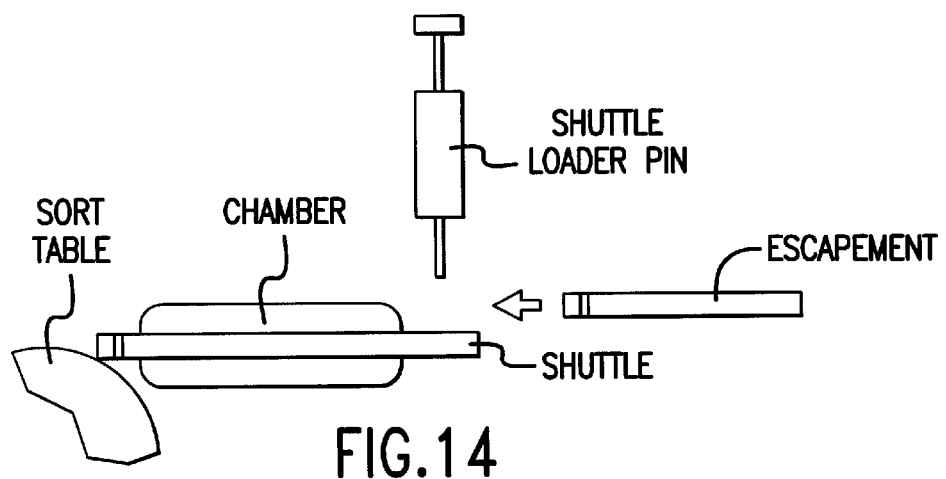

The sequence of operations of the apparatus is shown in FIGS. 9 to 14. As shown, the initial condition of the components is shown in FIG. 9 where the shuttle 120 and escapement slide 32 are both retracted (positions A and #1, respectively). In FIG. 10, the escapement slide 32 has been loaded with a seed and advanced to the unloader position #2. In FIG. 11, the unloader pin 128 has pushed the seed from the escapement slide 32 into the shuttle 120. In FIG. 12, the escapement slide 32 is moved back to position #1 ready for another seed. In FIG. 13, the shuttle 120 has been advanced into the dose calibrator to position B where the seed activity will be assayed. Finally, in FIG. 14, the shuttle has been advance to position C where the seed is unloaded into the correct pig 26 on the sort table 28.

Figure 15:
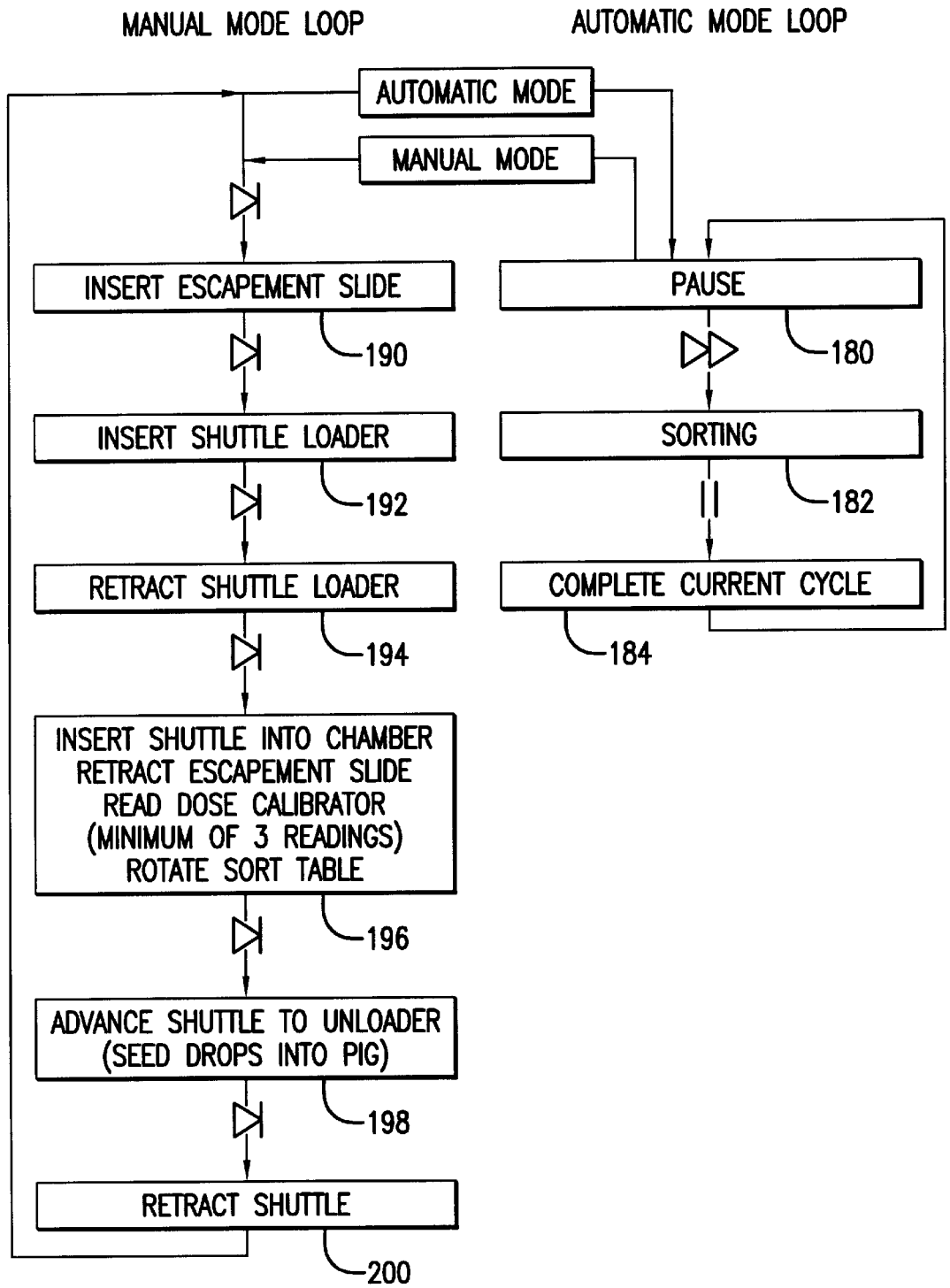
FIG. 15 is a block diagram showing the manual mode and the automatic mode of the apparatus.

The apparatus is capable of both manual mode and automatic mode of operation as depicted in the block diagram of FIG. 15. As shown, when the automatic mode is selected, the sorting is effected for an entire cycle, the steps of the automatic mode being pause 180, sorting 182 and complete current cycle 184. When the manual mode is selected, the steps are insert escapement slide 190, insert shuttle loader 192, retract shuttle loader 194, insert shuttle into the chamber, retract escapement slide, read dose calibrator (minimum of 3 readings), and rotate sort table, collectively step 196, advance shuttle to unloader (seed drops into pig) 198 and retract shuttle 200.

Figure 16A:
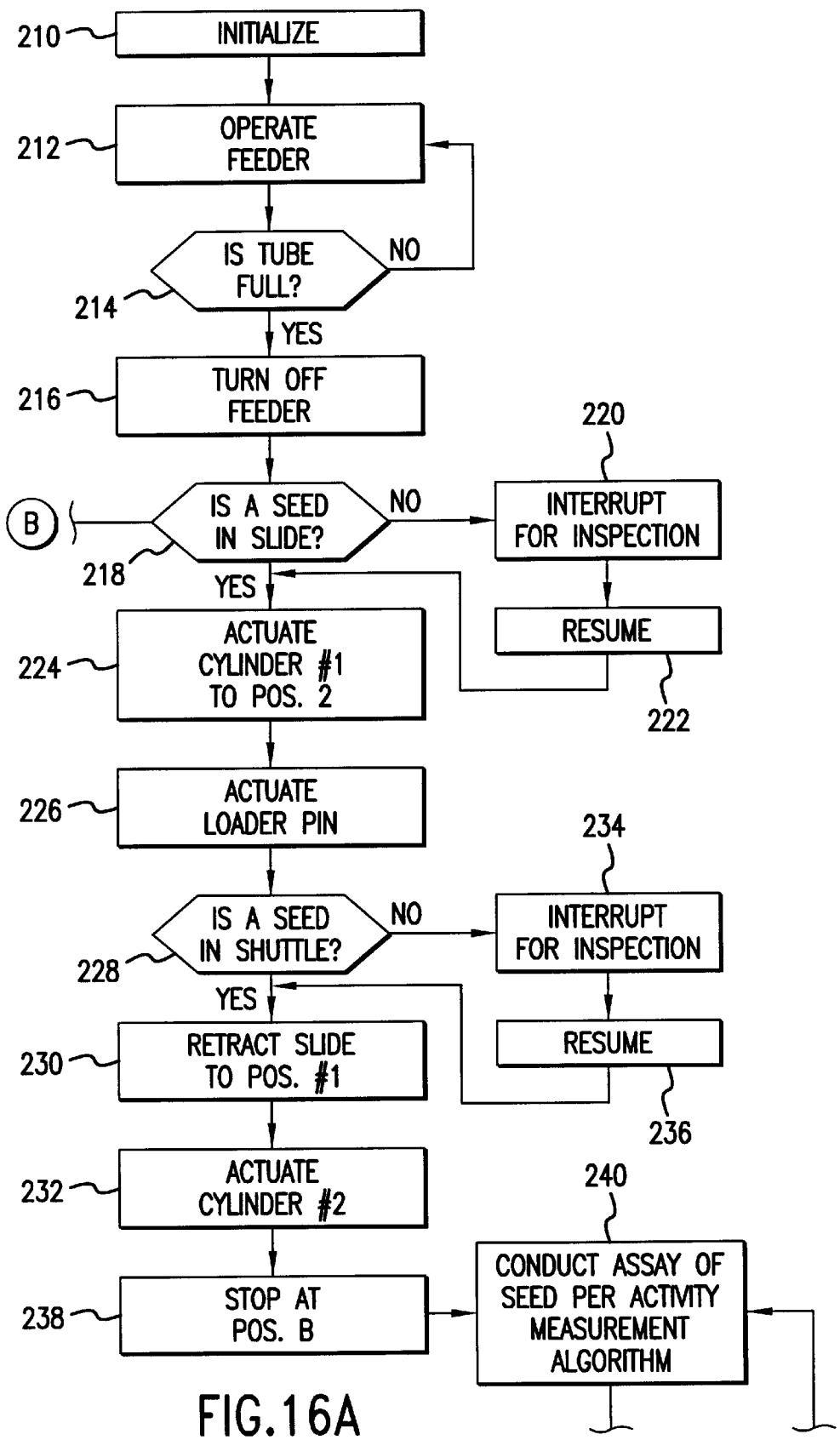
FIGS. 16a and 16b are a flowchart showing the operation of the apparatus and method.
Figure 16B:
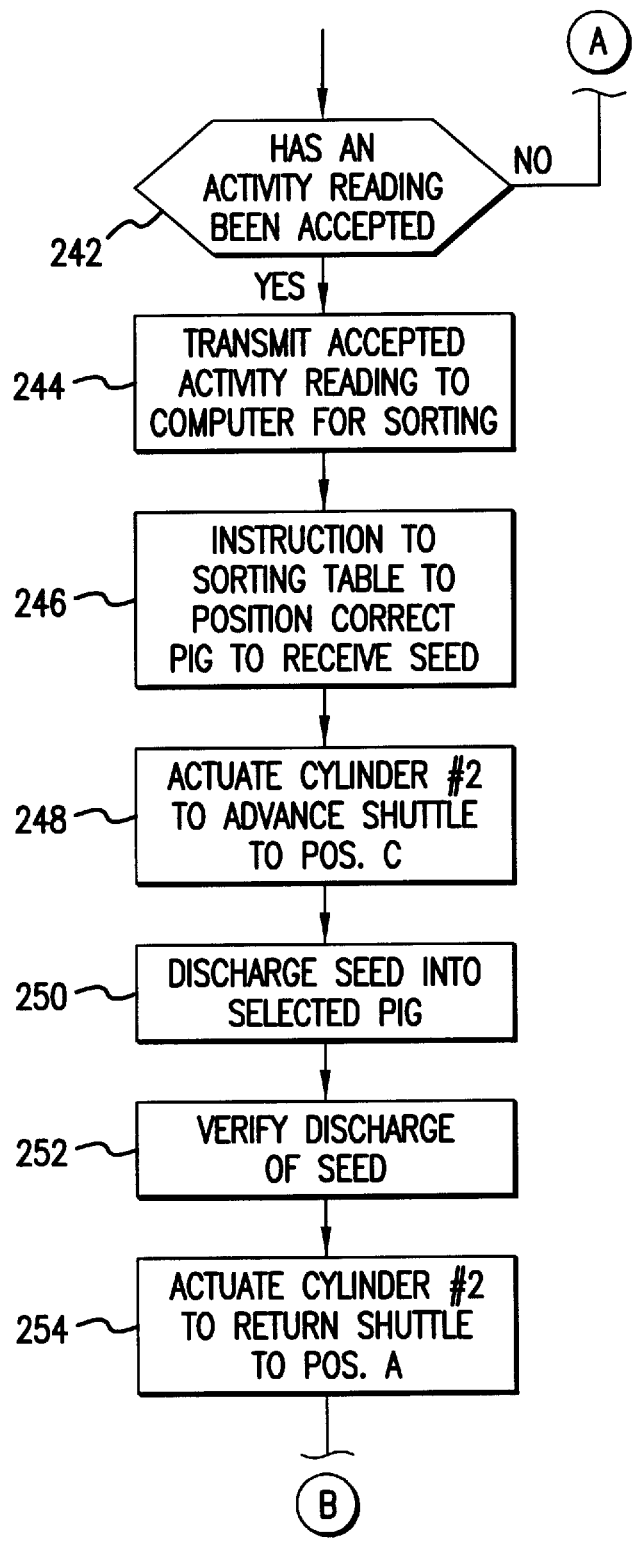

A flow chart of the method is shown in FIGS. 16*a* and FIG. 16*b*. In step 210 the apparatus is initialized. In step 212 the feeder 40 is operated to initiate a feed of seeds to the curved track 44. In step 214 the curved track 44 is interrogated to determine if the track is full to the required degree. If not, then the feeder 40 is continued to operate until the answer is yes, in which case the feeder 40 is turned off in step 216. Next the escapement 30 is interrogated in step 218 to determine if a seed is in the slide 32. If no, then the program is interrupted in step 220 for an inspection and correction. The program is resumed in step 222 when correction has been effected. In step 224, cylinder #1 (60) is actuated to position #2. In step 226, the unloader pin 128 is actuated to transfer the seed to the shuttle 120. In step 228, the shuttle 120 is interrogated to determine if a seed is in the shuttle. If the answer is yes, the slide 32 is retracted in step 230 and the cylinder #2 (62) is actuated in step 232 to advance the shuttle 120 from position A to position B. If the answer is no, then there is an interrupt and inspection in step 234. Once correction has been effected, the program is resumed in step 236 and steps 230 and 232 are performed. The cylinder #2 stops at position B in step 238. The seed assay is conducted in step 240 using the activity measurement algorithm. In step 242, a determination is made whether an activity reading has been accepted. If no, the program loops back to step 240. If yes, the program continues to step 244 where the activity reading is sent to the computer 80 for sorting. In step 246, the computer instructs the sorting table 28 to position itself for receiving the seed in the correct pig 26. In step 248, the cylinder #2 is advanced to position C. In step 250, the seed is discharged into the correct pig 26. In step 252, seed discharge is verified. In step 254, cylinder #2 is returned to position A, and the program loops back to step 218 and continues until all seeds have been assayed and sorted.

Figure 18A:
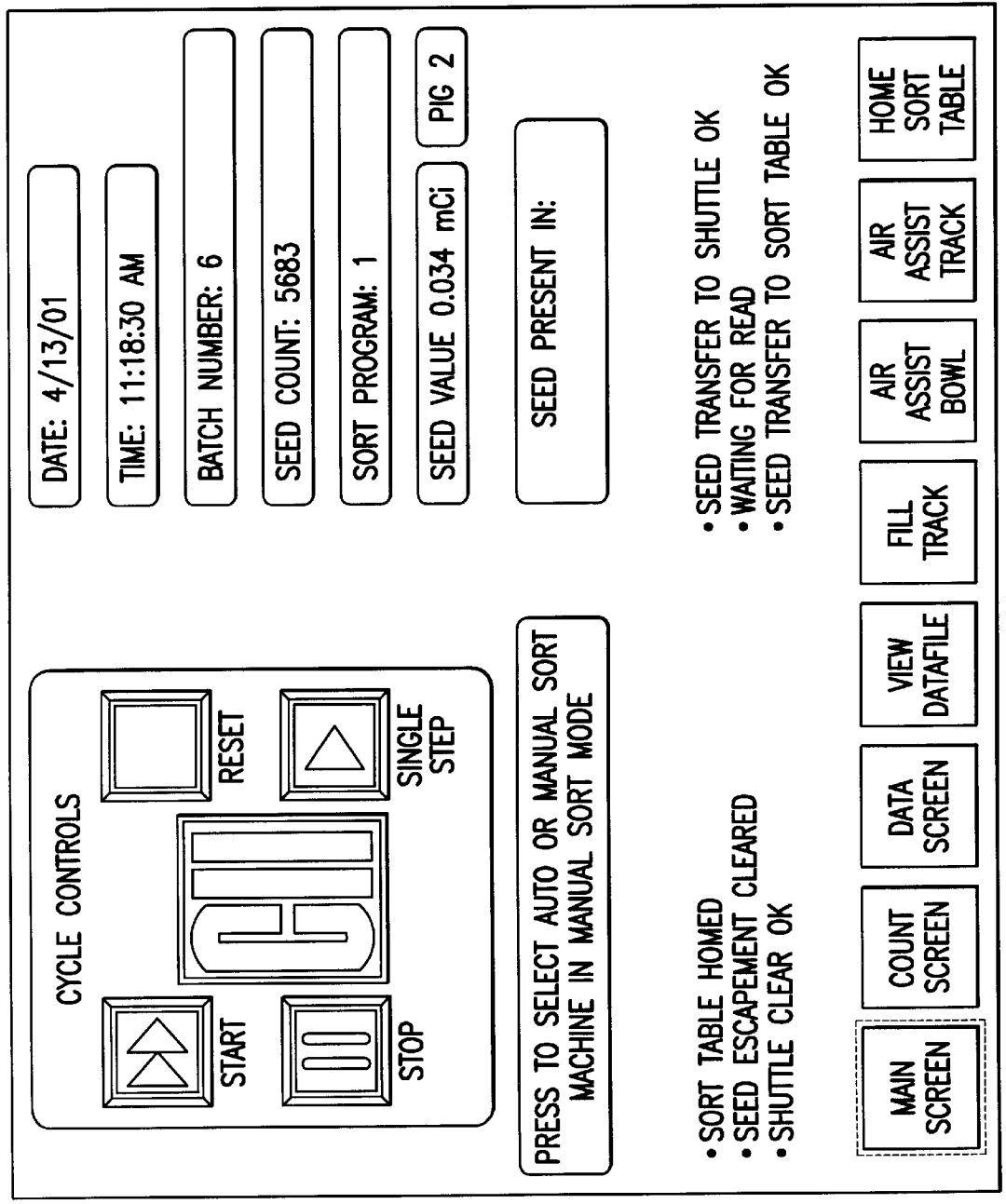
Figure 18B:
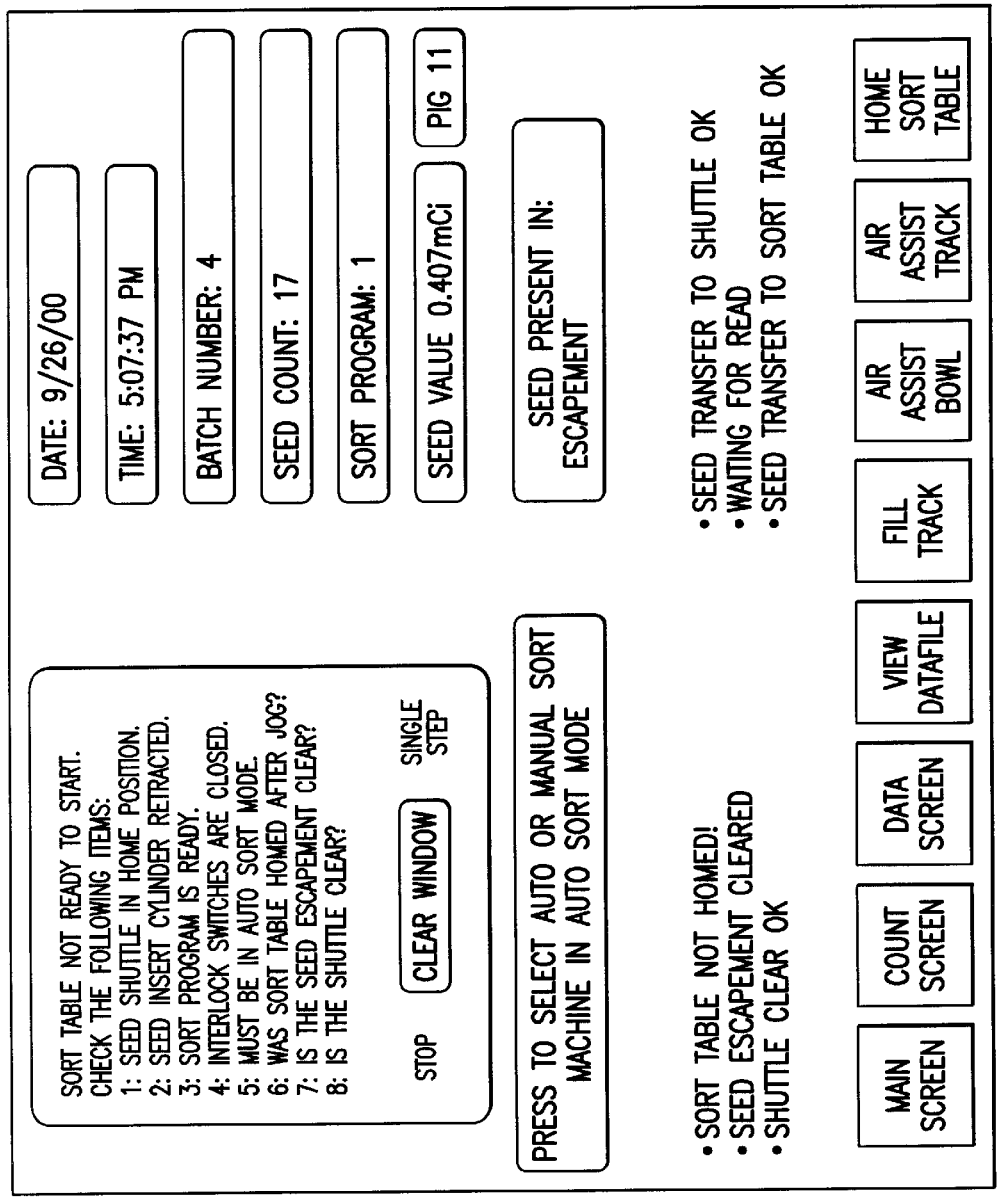

Typical display screens of the computer 80 are shown in FIGS. 18*a*, 18*b* and 18*c*. The indicia on the screen have the following meaning in relation to the program and apparatus. Batch and Seed Data: Indicators on the top-right of the Main Screen indicate data about the current batch, sort program selected, total seeds sorted, and the last seed measured. Seed Location: The presence and proper positioning of a seed in the escapement and the shuttle (determined by photosensors) is indicated in the box on the lower right side of the screen. The sorter will pause and wait for a seed to be detected in the escapement before proceeding with any activity. Sort Table Homed: A red circle indicates that the sort table is not homed—operation of the sorter is not permitted. Pressing the home sort table button on the control bar will clear this condition. Pressing the home sort table button is necessary if an error appears. Seed Escapement Cleared: Indicates that the escapement has retracted, and was cleared when retracted. If the escapement is retracted but not cleared, the operation of the sorter will stop. This is likely to indicate dirt or particle blocking the photosensor. If there is foreign material blocking the escapement, it is possible that a seed will not be properly inserted into the escapement (e.g., top could protrude above escapement), and could shear. Shuttle Clear OK: Indicates that the shuttle has retracted, and is clear (before loading). If the shuttle is not clear after retracting, the operation of the sorter will stop. This is likely to indicate dirt or particle blocking the photosensor. If there is foreign material blocking the shuttle, it is possible that a seed will not be properly inserted into the escapement, and could be damaged by the inserter pin.

Seed Transfer to Shuttle OK: Indicates that a seed was properly loaded into the shuttle (shuttle photosensor blocked). If the seed does not block the optical path at the base of the shuttle, it may have not have loaded properly. Waiting for Read/Good Read: Indicates that a steady reading was obtained from the dose calibrator. If a stable reading is not obtained within 20 read attempts, the system times out, and the green indicator turns red. Seed Transfer to Sort Table OK: After the shuttle advances to the unloader, the seed drops past a photosensor to ensure that it is deposited into the pig. If a seed is not detected, indicator will turn red and the system will stop. The seed counter will not increment if a seed drop is not detected.

There are 3 main screens that control operation of the Seed Sorter. Main Screen: has cycle controls; Count Screen: displays summary data about sorting progress (shown in FIG. 18*b*); and Data Screen: where sort programs are displayed and selected. There is also a control bar at the bottom of the screen that is present for all screens. The control bar switches between the screens. The buttons functions are:

Main Screen: switch to Main screen; Count Screen: switch to Count screen; Data Screen: switch to Data screen; View Datafile: display batch raw data file up to and including the last seed processed; Fill Track: activate feeder bowl to fill curved track; Air Assist Bowl: provide an air blast at the nose piece of the feeder bowl, used if seeds are misaligned and not readily entering the track; Air Assist Track: provide an air blast at the beginning of the curved track to nudge seeds down the track, if necessary (use if seed is not present in escapement); and Home Sort Table: if sort table is jogged, or an e-stop is created, this button will home the stepper motor used to drive the sort table. A typical Main Screen is shown in FIG. 18a, and a typical Data Screen is shown in FIG. 18c.

What is claimed is:

1. Apparatus for assaying and sorting radioactive seeds comprising:

a. a seed feeder having an outlet to feed seeds out the outlet in line horizontally in end to end fashion;
 b. a curved track having a horizontal inlet coupled to the outlet of the seed feeder and having a vertical outlet so seeds can drop by gravity out the vertical outlet;
 c. an escapement slide having a first cavity to receive a seed positioned below the vertical outlet of the curved track, the escapement slide reciprocating between a first position where the first cavity is in vertical alignment with the vertical outlet of the curved track and a second position where the slide has been shifted horizontally;
 d. a shuttle loader located at the second position of the slide comprised of a vertically oriented loader pin arranged for reciprocating vertical movement between a retracted position and a loading position, with the loader pin in vertical alignment with the first cavity of the slide when it is in the second position;
 e. a shuttle located below the slide and arranged to move horizontally from a first retracted position, to an intermediate position and to an unloader position, the shuttle having a second cavity that is in vertical alignment with the loader pin when the shuttle is in the first retracted position;
 f. a dose calibrator in alignment horizontally with the shuttle to receive the shuttle in its intermediate position and determine the activity of a seed contained in the second cavity, and to allow the shuttle to pass through when moved to the unloader position;
 g. a bridge supporting the shuttle and extending from the first retracted position to the unloader position and defining a hole that is vertically aligned with the shuttle second cavity when the shuttle is in the unloader position to allow a seed in the shuttle to drop through the hole by gravity;
 h. a sort table having a series of concentrically mounted receptacles, the sort table capable of being positioned with any one of the receptacles vertically below the hole in the bridge to receive a seed dropping through the hole by gravity; and
 i. a processor coupled to the dose calibrator and sort table to process the activity determined by the dose calibrator and to instruct the sort table to position a preselected receptacle beneath the hole in the bridge to receive the seed whose activity was determined.

2. Apparatus for assaying and sorting radioactive seeds according to claim 1 wherein the curved track has a vertical terminal portion and a sensor is associated with the curved track to determine the presence of seeds to a predetermined level in the vertical terminal portion of the curved track.

3. Apparatus for assaying and sorting radioactive seeds according to claim 1 wherein a sensor is associated with each of the first cavity and second cavity, each sensor determining the presence of a seed respectively associated cavity.

4. Apparatus for assaying and sorting radioactive seeds according to claim 1 wherein piston-cylinder assemblies are provided coupled to drive the slide and shuttle.

5. Apparatus for assaying and sorting radioactive seeds according to claim 4 wherein sensors are associated with the piston-cylinder assemblies to control the actuation thereof.

6. Apparatus for assaying and sorting radioactive seeds according to claim 1 wherein the bridge has a cutout at the location corresponding to the intermediate position of the shuttle.

7. Apparatus for assaying and sorting radioactive seeds according to claim 1 wherein the dose calibrator is of annular configuration.

8. Apparatus for assaying and sorting radioactive seeds according to claim 1 wherein the feeder includes a track leading to the feeder outlet with the track having a cutout adjacent to the outlet and an air assist is provided to cooperate with the feeder in the vicinity of the outlet to maintain seeds in a single line.

9. Apparatus for assaying and sorting radioactive seeds according to claim 1 wherein an air assist is provided to cooperate with the curved track.

10. Apparatus for assaying and sorting radioactive seeds according to claim 1 wherein an air jet is positioned over the hole defined in the bridge.

11. Method for assaying and sorting radioactive seeds comprising the steps of:

a. feeding seeds in line horizontally in end to end fashion;
 b. translating the seeds from the horizontal to a vertical stack;
 c. singulating the seeds from the vertical stack and moving a singulated seed to a horizontally displaced position;
 d. loading the horizontally displaced singulated seed into a shuttle by pushing vertically downward into a cavity in the shuttle;
 e. moving the shuttle horizontally from a retracted position where it receives a singulated seed, into one end of an annular dose calibrator to an intermediate position within the dose calibrator and out of the other end of the annular dose calibrator to an unloader position;
 f. determining the activity of the singulated seed contained in the cavity while it is in the intermediate position;
 g. dropping the singulated seed into one of a plurality of receptacles at the unloader position; and
 h. controlling the plurality of receptacles to position a preselected receptacle to receive the singulated seed based on the activity determined.

12. Method for assaying and sorting radioactive seeds according to claim 11 including the further step sensing the presence of seeds in the vertical stack.

13. Method for assaying and sorting radioactive seeds according to claim 11 including the further steps of sensing a seed when initially singulated and sensing a singulated seed in the shuttle.

14. Method for assaying and sorting radioactive seeds according to claim 11 including the steps of driving the initially singulated seed to the horizontally displaced position and driving the shuttle between its positions.

15. Method for assaying and sorting radioactive seeds according to claim 14 including the further step of controlling the driving of the initially singulated seed and shuttle.

16. Method for assaying and sorting radioactive seeds according to claim 11 including the further step of supporting the shuttle at the intermediate position with a reduced section.

17. Method for assaying and sorting radioactive seeds according to claim 11 including the step of blowing air into the seeds during translation from the horizontal to the vertical.

18. Method for assaying and sorting radioactive seeds according to claim 11 including the further step of blowing air at the seeds to assist in maintaining the horizontal in line feeding of seeds.

19. Method for assaying and sorting radioactive seeds according to claim 11 including the further step of blowing air toward the singulated seed to assist in the step of dropping the singulated seed into a receptacle.

20. Method for assaying and sorting radioactive seeds according to claim 11 including the further step of sensing the dropping of a singulated seed into a receptacle.

* * * * *